United States Patent
Markaverich et al.

(10) Patent No.: US 6,277,418 B1
(45) Date of Patent: Aug. 21, 2001

(54) CORN EXTRACT CONTRACEPTIVE

(75) Inventors: Barry M. Markaverich, The Woodlands; Robert Faith; Shaila Mani, both of Houston, all of TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 09/311,751

(22) Filed: May 14, 1999

Related U.S. Application Data

(60) Provisional application No. 60/087,680, filed on Jun. 2, 1998.

(51) Int. Cl.$^7$ .................................................. A61K 35/78
(52) U.S. Cl. ............................................ 424/750; 514/841
(58) Field of Search ................................ 424/195.1, 750; 514/841

(56) References Cited

U.S. PATENT DOCUMENTS 4,950,481 * 8/1990 Keri et al. .......................... 424/195.1

FOREIGN PATENT DOCUMENTS

| | | | |
|---|---|---|---|
| 8102022 | * | 10/1997 | (JP) . |
| 9122146 | * | 8/1998 | (JP) . |
| WO 92/03142 | | 3/1992 | (WO) ............................ A61K/35/78 |

OTHER PUBLICATIONS

Kraft, "The Manufacture, Shipping and Receiving and Quality Control of Rodent Bedding Materials," *Laboratory Animal Care*, vol. 30, No. 2, pp. 366–376 (1980).

Port, et al., "The Effect of Corrncob Bedding on Reproductivity and Leucine Incorporation in Mice," *Laboratory Animal Care*, vol. 19, No. 1, pp. 46–49 (1969).

Iturrian, et al., "Comparison of Bedding Material: Habitat Preference of Pregnant Mice and Reproductive Performance," *Laboratory Animal Care*, vol. 18, No. 2, pp. 160–164 (1968).

Clark, et al., "Effect of Estradiol–17α on Nuclear Occupancy of the Estrogen Receptor, Stimulation on Nuclear Type II Sites and Uterine Growth," *J. Steroid Biochem.*, vol. 16, pp. 323–328 (1982).

Clark, et al., "The Agonistic and Antagonistic Actions of Estriol," *J. Steroid Biochem*, vol. 20, No. 4B, pp. 1005–1013 (1984).

Markaverich, et al., "Two Binding Sites for Estradiol in Rat Uterine Nuclei: Relationship to Uterotropic Response," *Endocrinology*, vol. 105, No. 6, pp. 1458–1462 (1979).

Noble, et al., "Spontaneous and Estrogen–produced Tumors in Nb Rats and Their Behavior after Transplantation," *Cancer Research*, vol. 35, pp. 766–780 (Mar. 1975).

Markaverich, et al., "The Effect of Low Dose Continuous Exposure to Estradiol on the Estrogen Receptor (Type I) and Nuclear Type II Sites," *Endocrinology*, vol. 114, No. 3, pp. 814–820 (1984).

Markaverich, et al., "Effects of Coumestrol on Estrogen Receptor Function and Uterine Growth in Ovariectomized Rats," *Environmental Health Perspectives*, vol. 103, No. 6, pp. 574–581 (Jun. 1995).

Marcelli, et al.,"Altered Growth and Insulin–Like Growth Factor–Binding Protein–3 Production in PC3 Prostate Carcinoma Cells Stably Transfected with a Constitutively Active Androgen Receptor Complementary Deoxyribonucleic Acid," *Endocrinology*, vol. 136, No. 3, pp. 1040–1048 (1995).

Markaverich, et al., "Heterogeneity of Nuclear Estrogen–Binding Sites in the Rat Uterus: A Simple Method for the Quantitation of Type I and Type II Sites by [$^3$H] Estradiol Exchange," *Endocrinology*, vol. 109, No. 1, pp. 62–69 (1981).

* cited by examiner

Primary Examiner—Christopher R. Tate
(74) Attorney, Agent, or Firm—Brobeck, Phleger & Harrison LLP

(57) ABSTRACT

Novel compositions extracted from corn products provide contraceptive and anti-neoplastic activities. Using novel extraction procedures, compositions may be isolated from corn products. For example, a *Zea mays* plant product is extracted in a first solvent to produce a solvent extract, the solvent extract is dried to produce an extracted solid, the extracted solid is solubilized in a second solvent, the solubilized extract is purified in a chromatographic process, and an active fraction is collected from the chromatographic process. Compositions may be applied to animal bedding or food, and are adaptable to any suitable method of administration. The contraceptive activity of these compositions is effective for both males and females.

27 Claims, 21 Drawing Sheets

CORN EXTRACT CONTRACEPTIVE

REFERENCE TO RELATED APPLICATIONS

This application claims the benefit of U.S. Provisional Patent Application No. 60/087,680, filed Jun. 2, 1998.

BACKGROUND OF THE INVENTION

1. Field of the Invention

This invention relates to pharmaceutical compositions derived from corn extracts useful as contraceptive compositions and antineoplastic compositions.

2. Description of the Background

Contraception is often desired to control reproduction. While a plurality of contraceptive compositions and methods are available commercially, most methods of chemical contraceptives are active through a limited number of pathways. Thus, the majority of contraceptive compositions still involve the use of one or more natural or synthetic hormones such as estrogen, progestin and ethinyl estradiol.

While natural and synthetic hormones are effective, their use has not been without substantial and undesirable side effects. Numerous side effects have been associated with the use of natural or synthetic hormones in contraceptives, such as, for example, thrombophlebitis, thrombosis, pulmonary embolism, coronary thrombosis, myocardial infarction, cerebral thrombosis, cerebral hemorrhage, hypertension, irregular bleeding, and irregular menstrual cycle.

Even with the reduction (but not elimination) of side effects through improved formulation, a number of disadvantages are still associated with current contraceptive compositions. Oral contraceptives rely on a high degree of patient compliance. For example, the risk of pregnancy increases with each pill missed or each pill taken out of order. Also, implantable contraceptives have many undesirable side effects and enjoy limited consumer acceptance. Another disadvantage of conventional contraceptives is that they are only effective when taken by females. Thus, the type of contraceptive choices available to couples is limited.

SUMMARY OF THE INVENTION

The present invention overcomes many of the limitations, problems and disadvantages associated with current strategies and designs for contraception and provides compositions and methods for contraception. As embodied and broadly described herein, the present invention is directed to a corn extract, such as an extract from corn cob, useful as a contraceptive. In addition, extracts of the present invention are also useful as antineoplastic agents.

One embodiment of the invention is directed to a process for producing a therapeutic substance. In this process, a Zea mays plant product is extracted to produce a solvent extract, the solvent extract is dried to produce an extracted solid, the extracted solid is resolubilized in a solvent to form a resolubilized extract, the resolubilized extract is purified in a chromatography process, such as a reverse phase column chromatography process, and an active fraction is collected from the chromatography process. The Zea mays plant product used for starting material may be corn kernel, corn cob, animal bedding material made from corn cob, and mixtures of these materials.

Another embodiment of the invention is directed to a therapeutic substance produced by the process of the invention. The therapeutic substance may be in the form of a salt, a compound, a complex or a combination of these forms.

Another embodiment of the invention is directed to a pharmaceutical preparation that contains the therapeutic substance produced by the process of this invention.

The pharmaceutical preparation may include, in addition to the active ingredients, a pharmaceutically acceptable carrier.

Another embodiment of the invention is directed to a composition for effecting contraception in a patient. The composition is preferably made using the process of the invention. The patient may be any mammal such as, for example, humans, monkeys, mice, rats, guinea pigs, rabbits, hamsters, horses, cattle, pigs, sheep, goats, dogs and cats.

Another embodiment of the invention is directed to a method of contraception comprising isolating an extract from a Zea mays plant product using a polar solvent and administering an effective amount of the extract to an individual to effect contraception.

Another embodiment of the invention is directed to a method for treating a patient with a neoplastic disorder comprising administering to the patient an antineoplastic composition comprising an effective quantity of the therapeutic compound of the invention. The antineoplastic composition of the invention may further comprise an antineoplastic compound or agent, which may be, for example, methotrexate.

Another embodiment of the invention is directed to a method of inhibiting neoplastic activity comprising the steps of isolating an antineoplastic extract from a Zea mays plant product using a polar solvent and administering an effective amount of the antineoplastic extract to an individual. The method may further comprise the step of administering an antineoplastic compound, such as methotrexate.

Another embodiment of the invention is directed to an isolated and purified compound derived from an extract of Zea mays having a molecular weight of 348 amu. Preferably, the compound is isolated from extract that is derived from Zea mays corn cob using a polar solvent.

Another embodiment of the invention is directed to an isolated and purified compound derived from an extract of Zea mays having a molecular weight of 353 amu. Preferably, the compound is isolated from extract that is derived from Zea mays corn cob using a polar solvent.

Another embodiment is directed to an isolated and purified compound derived from an extract of a Zea mays plant product, the extract being derived from the Zea mays plant product according to the methods of the invention, the compound eluting as a single UV-absorption peak from a $C_{18}$ reversed phase HPLC column having a flow rate of 2 ml per minute, as described below, the compound eluting approximately 56 minutes after injection of the extract sample onto the column, and having a molecular weight of either 348 amu or 353 amu.

Another embodiment is directed to an isolated and purified compound derived from an extract of a Zea mays plant product, the extract being derived from the Zea mays plant product according to the methods of the invention, the compound eluting as a single UV-absorption peak from a $C_{18}$ reversed phase HPLC column having a flow rate of 2 ml per minute, as described below, the compound eluting approximately 60 minutes after injection of the extract sample onto the column, and having a molecular weight of either 348 amu or 353 amu.

Other embodiments and advantages of the invention are set forth, in part, in the description which follows and, in part, will be obvious from this description and may be learned from the practice of the invention.

DESCRIPTION OF THE INVENTION

Figure 1:
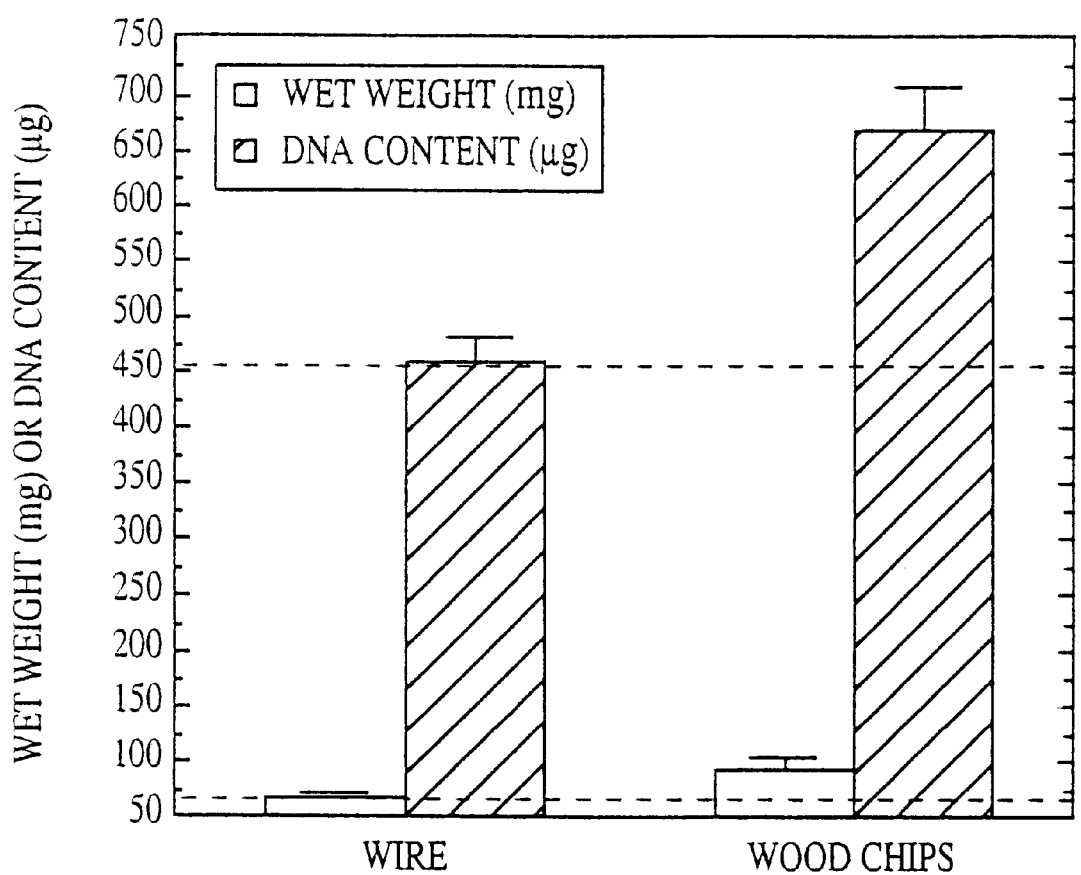
FIG. 1 Uterine wet weight and DNA content of ovariectomized rats housed on wire bedding or estrogenic substance-containing wood chip bedding for 14 days.

This invention is directed to corn extracts and uses of compositions derived from corn extracts. Corn, also know as *Zea mays*, maize, or maiz, may be any of numerous cultivated forms of usually tall annual cereal grass bearing grains or kernels on large ears.

The present invention is also directed to a process for producing a therapeutic substance from a *Zea mays* plant product. The therapeutic substance may be a substance that shows contraceptive activity or antineoplastic activity or a combination of both activities. Compositions of the invention are useful for the control of sexual behavior in both males and females and may function as a chemical substitute for surgical castration. Potential uses of the invention include its use in a composition for blocking lordosis, an environmentally safe contraceptive for pest population control and a food additive with contraceptive activity.

Contraceptive activity may be any activity that diminishes the likelihood of, or prevents conception. Contraceptives may work through many mechanisms including: (1) inhibiting the estrous cycle in females; (2) inhibiting estrus (the recurrent, restricted period of sexual receptivity in female mammals, other than humans, characterized by intense sexual urge); (3) blocking ovulation or prevention of normal egg formation in the female; (4) the reduction of sexual desire or behavior in the male or female; (5) blocking, reducing, or preventing formation of normal sperm in the male; (6) inducing erectile dysfunction in the male; and (7) inhibiting post fertilization implantation of the zygote. Further, contraceptives may work by a combination of any of the above mechanisms.

Antineoplastic activity may be any activity that inhibits or prevents the development of neoplasms or any activity that would check the maturation or proliferation of malignant cells. Inhibition of neoplasm may be due to an anti-hypertrophic (the prevention of the enlargement or overgrowth of an organ or part due to an increase in size of its constituent cells) or anti-hyperplastic (the prevention of abnormal multiplication or increase in the number of normal cells in normal arrangement in a tissue) activity as the antineoplastic activity.

The antineoplastic activity may be a direct result of the therapeutic substance of the *Zea mays* plant product, or alternately, the antineoplastic activity may be only present when the therapeutic substance of *Zea mays* is combined with another therapeutic substance.

For example, a therapeutic substance may selectively induce the growth of neoplastic cells such that they are more susceptible to the effects of antimitogenic chemotherapeutic substances.

The starting material for extraction of the therapeutic substance is *Zea mays*, which is also known as poaceae, corn, maize, mealie and indian corn. *Zea mays* refers to any annual grass of the grass order Cyperales, family Zea and genus *mays* and includes all cultivars in the *mays* family such as everta (popcorn), indurata (flint corn), indents (dent corn), amylacea (flour corn), saccharata (soft corn, sweet corn) and tunicata (pod corn).

Corn kernel or corn seed are the common names for what is technically the fruit of *Zae mays*. The *Zea mays* plant part or product which may be used for extraction may include, for example, the corn cob or the corn kernel. The starting material may be fresh, frozen, dried, or preserved *Zea mays* plant parts or products and mixtures thereof. Dried forms of Zea mays plant product include dried ground corn cob bedding (GCCB) which is commercially sold under the trade name BEDOCOB™. The animal bedding material may be any commercially available ground corn cob bedding material.

The therapeutic substance may be extracted from the *Zea mays* plant parts or products by solvent extraction followed by drying to produce an extracted solid. The extracted solid may be resolubilized in solvent before use. The solvent used for extraction and solubilization may be the same. Alternatively, the extracted solid may be further purified by reverse phase chromatography. In reverse phase chromatography, fractions eluted from a column are collected and tested for activity.

Solvent extraction may be performed using any primary, secondary and tertiary alcoholic solvent such as methanol, ethanol, propanol, butanol, sec butyl alcohol and mixtures of these alcohols. The solvent used for extraction may also be selected from the group consisting of alcohols, ethers, ketones, water and mixtures thereof. In a preferred embodiment, the solvent is the alcohol methanol.

Extraction may be performed using standard extraction procedures such as those listed in the Examples section or in Protein Purification (R.K. Scopes, 2nd edition, Springer-Verlag, New York, 1987). The extraction may be performed under room temperature or at a temperature of between about 0° and about 100° C. and may be performed for about 1 hour to about 1 month. In one embodiment of the invention, corn cob, corn kernel or corn on the cob (or mixtures thereof) is immersed in an alcohol such as methanol in an enclosed chamber for a period of time of between one hour to one month. The starting material may be whole or may be processed to a small size more convenient for extraction.

The temperature of the alcohol may be controlled between 0° C. and 100° C.

After extraction, the liquid phase of the extraction is separated from the solid phase. Separation may be by any commonly known method such as filtering, settling, and centrifugation. After the separation, the mixture may be dried to form a dried extract. Drying may be performed by vacuum evaporation such as in a centrifugal vacuum evaporator, by exposure to dry air such as dried nitrogen, by lyophilization, or by evaporation with or without the assistance of heat. The solid extract may be resolubilized in a suitable solvent such as, for example, dimethyl sulfoxide (DMSO), methanol, water or mixtures of these chemicals.

One preferred purification method for the purification of the therapeutic substance is reverse phase chromatography including reverse phase high performance liquid chromatography (reverse phase HPLC). Reverse-phase HPLC may be performed using hydrophobic adsorbents such as short-chain aliphatic groups attached to the matrix, and increasing organic solvent concentrations to elute. A preferred hydrophobic absorbent is a $C_{18}$ solid phase and a preferred hydrophilic solvent is a mixture of methanol and water. In a preferred embodiment, the method of reverse phase chromatography uses a $C_{18}$ solid phase column and the active fraction is eluted from the column with a solution of about 80% methanol and about 20% water.

Chromatography may be performed in column or batch mode. In column chromatography, a sample is loaded onto the column and eluted with successively higher concentrations of a hydrophilic solvent. The increase in solvent hydrophobicity may be continuous, such as, for example, from 20% to 100% methanol in 100 ml of chromatography liquid. Alternatively, the increase in solvent hydrophobicity may be discrete, such as, for example, loading with water and 20% methanol, elution with 40% methanol in water, 60% methanol in water, 80% methanol in water and 100% methanol. Other purification methods which may be used in addition to reverse phase chromatography include low pressure column chromatography, batch chromatography, precipitation, specific adsorbent chromatography, gel filtration, HPLC and combinations of these methods.

In a preferred embodiment of the invention, the reverse phase column is loaded with 20% methanol in water and washed with 60% methanol in water and a fraction showing the desired contraceptive and antineoplastic activity is eluted with 80% methanol in water. While one elution condition has been disclosed, other elution conditions may be determined by one of ordinary skill in the art without undue experimentation. For example, a $C_8$ to $C_{18}$ column, such as columns like a $C_9$, $C_{10}$, $C_{11}$, $C_{12}$, $C_{13}$, $C_{14}$, $C_{15}$, $C_{16}$ or $C_{17}$ column may require different elution conditions than a $C_{18}$ column.

Another embodiment of the invention is directed to a therapeutic substance produced by the process of the invention. The therapeutic substance may have contraceptive or antineoplastic activities and may be in a form of a salt, a compound, a complex or a combination of these forms.

Another embodiment of the invention is directed to a pharmaceutical preparation comprising a therapeutic substance produced by the process of the invention with a pharmaceutically acceptable carrier. The pharmaceutical preparation may be in the form of an aqueous solution for parenteral and oral use, a capsule for oral use, or in other forms such as unguents, ointments, creams, suppositories and ovules. Administration routes may include parenteral, oral, ocular, periodontal, rectal or vaginal delivery, among others.

Another embodiment of the invention is directed to a composition for effecting contraception in a patient. The composition includes a contraceptive substance produced by the process of this invention. The patient may be a male or female mammal and may belong to any mammalian group including, but not limited to, hominids (humans), bovine, porcine, equine, caprine, canine, feline, murine and ovine groups. The methods and compositions of the present invention are useful for all types of laboratory animals, including those of the orders Rodentia (e.g. mice, rats, hamsters, guinea pigs, gerbils) Lagormorpha (e.g. rabbits) and Primates.

The contraceptive composition may be administered to a mammal by daily administration, weekly administration, monthly administration, yearly administration, continuous administration and cyclic administration. Methods of administration may be in the form of a pill or liquid capsule, an injection, a patch, a silastic implant or any other suitable means known in the art.

Another embodiment of the invention is directed to a method of contraception comprising isolating an extract from a *Zea mays* plant product using a polar solvent and administering an effective amount of the extract to an individual to effect contraception. The plant product is preferably selected from the group consisting of corn kernel, corn cob, animal bedding material made from corn cob, and mixtures thereof The step of isolating the extract may further comprise the step of purifying the extract by a chromatographic process before administration. In a preferred embodiment, the chromatographic process is reverse phase chromatography and the polar solvent is an alcohol.

The contraceptives and methods of contraception of the present invention may be used on both females and males. In females, contraception may be effected by inhibiting estrus, inhibiting the estrous cycle, inhibiting or blocking ovulation, inhibiting or blocking oogenesis, inhibiting or reducing sexual desire, inhibiting zygote implantation or combinations thereof. In males, contraception may be effected by inhibiting or reducing sexual desire, inhibiting, blocking, reducing or preventing spermatogenesis, inhibiting erectile function, or combinations thereof. The invention may be used on any male or female mammal selected from the group consisting of humans, monkeys, mice, rats, guinea pigs, rabbits, hamsters, horses, cattle, pigs, sheep, goats, dogs and cats. The extract may be administered to the individual by any suitable route of administration, including, but not limited to, orally, topically, intramuscularly, intravenously, subcutaneously, vaginally, rectally or by pulmonary absorption.

Another method of the invention is directed to a method for treating a patient with a neoplastic disorder comprising administering to the patient an antineoplastic composition which contains an effective quantity of the antineoplastic therapeutic compound of the present invention. The antineoplastic composition may further comprise an antineoplastic compound or agent, which may be, for example, methotrexate.

While all neoplasms may be treated with the therapeutic compounds of the invention, preferred neoplasms may be those that are responsive to antineoplastic agents, mitogen therapy or cell cycle specific agents such. These agents and mitogens may be used alone or in combination. Antineoplastic agents are known to those of skill in the art. Examples of antineoplastic agents which may be used alone or in combination include 5-fluorouracil, 6-mercaptopurine, 6-thioguanine, alkylating agents, androgens, antiadrenals, antiandrogens, antiestrogens, antimetabolites, asparaginase, bleomycin, busulfan, carboplatin, carmustine, chlorambucil, cisplatin, corticosteroids, cyclophosphamide, cytarabine, dacarbazine, dactinomycin, daunorubicin, doxorubicin, estrogens, etoposide, fludarabine, fluorouracil, flutamide, hexamethylmelamine, hormones, hydroxyurea, hypothalamic agents, idarubicin, ifosfamide, intrapleural, lomustine, mechlorethamine, melphalan, methotrexate, mithramycin, mitomycin, mitotic inhibitors, mitoxantrone, pacelitaxel, procarbazine, progestins, streptozocin, taxol, thiotepa, vinblastine, vincristine, vinorelbine and combinations and analogs thereof. Of these agents at least vincristine, vinblastine, vinorelbine, etoposide, pacelitaxel, methotrexate, 6-mercaptopurine, 6-thioguanine, fludarabine, 5-fluorouracil and cytarabine may be considered cell cycle specific agents. In a preferred embodiment, the antineoplastic compound is methotrexate.

Neoplasms which may be treated may be any cancer that responds to mitogen therapy or cell cycle specific agents such as: acute lymphocytic leukemia; non Hodgkin's lymphoma; and breast, testicular, gastrointestinal tract, lung, skin, head, and neck tumors. Other neoplasms which may be treated include bone cancer, liver cancer and pancreatic cancer, prostate cancer, lymphomas and testicular cancer.

Another embodiment of the invention is directed to a method of inhibiting neoplastic activity comprising the steps of isolating an antineoplastic extract from a *Zea mays* plant product using a polar solvent and administering an effective amount of the antineoplastic extract to an individual. The method may further comprise the step of administering an antineoplastic compound such as methotrexate. In a preferred embodiment, the neoplastic activity to be inhibited is breast cancer cell proliferation. The extract may be administered by any of numerous methods such as, for example, orally, topically, intramuscularly, intravenously, subcutaneously, vaginally, rectally or by pulmonary absorption.

Figure 21:
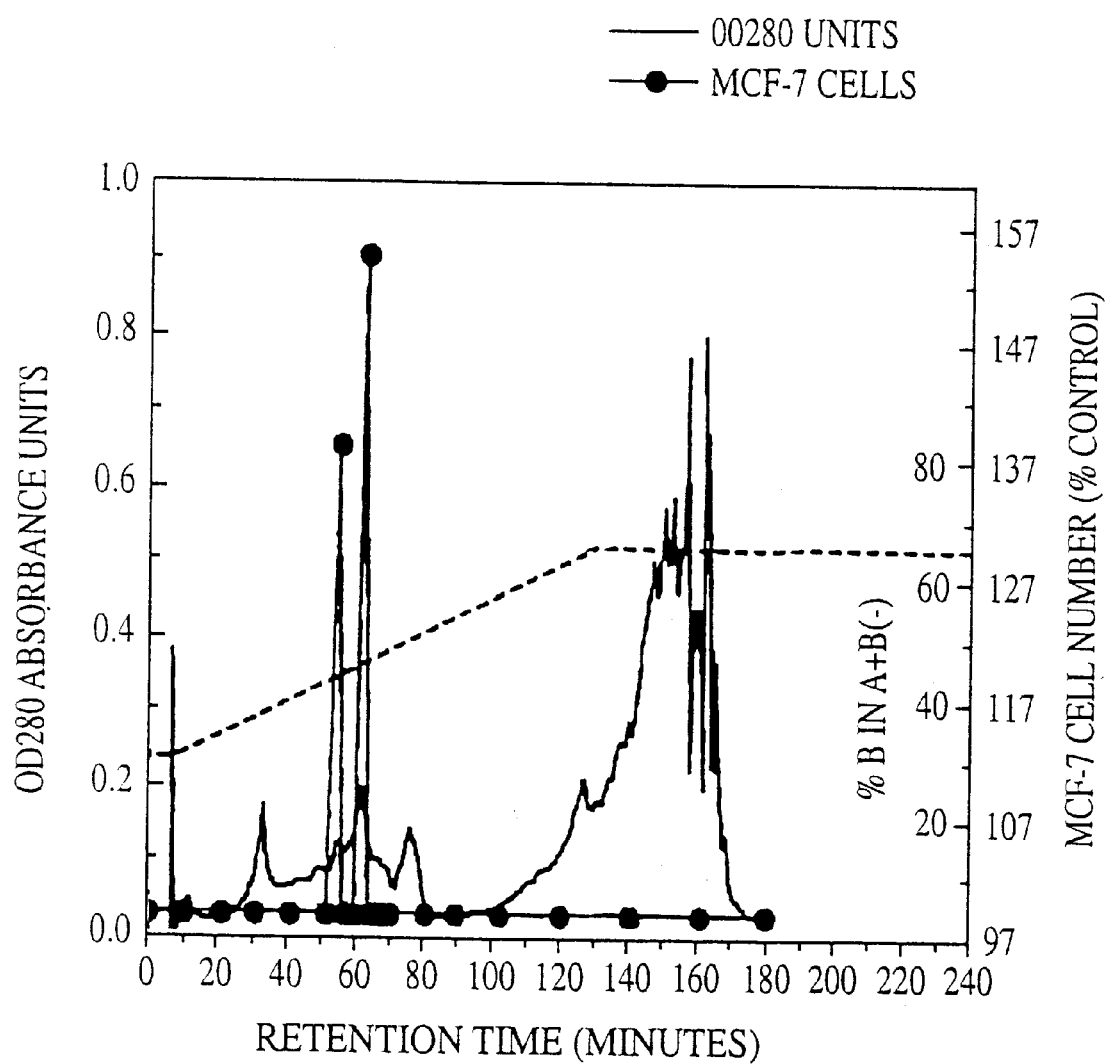
FIG. 21 HPLC purification of a corn cob mitogen.

Another embodiment of the invention is directed to an isolated and purified compound derived from an extract of *Zea mays*. A *Zea mays* extract is prepared according to the methods of the present invention. The isolated and purified compound is then purified from the extract using a semi-preparative $C_{18}$ reversed phase HPLC column equilibrated in 70% water and 30% acetonitrile containing 0.05% acetic acid, at a flow rate of 2 ml per minute at the time of sample injection. Ten minutes following the sample injection, the extract is eluted from the column with a linear gradient of acetonitrile (30% to 65%) in water (70% to 35%) containing 0.05% acetic acid which increases over a 120 minute period. The target compound elutes as a single UV-absorption peak approximately 56 minutes following injection (FIG. 21). As discussed in the examples which follow, this isolated and purified compound has a molecular weight of either 348 or 353 amu.

Another embodiment of the invention is directed to another isolated and purified compound derived from an extract of *Zea mays*. As with the previous compound, a *Zea mays* extract is prepared according to the methods of the present invention. The isolated and purified compound is then purified from the extract using a semipreparative $C_{18}$ reversed phase HPLC column equilibrated in 70% water and 30% acetonitrile containing 0.05% acetic acid, at a flow rate of 2 ml per minute at the time of sample injection. Ten minutes following the sample injection, the extract is eluted from the column with a linear gradient of acetonitrile (30% to 65%) in water (70% to 35%) containing 0.05% acetic acid which increases over a 120 minute period. The target compound elutes as a single UV-absorption peak approximately 60 minutes following injection (FIG. 21). As discussed in the examples which follow, this isolated and purified compound has a molecular weight of either 348 or 353 amu.

Although chromatographic behavior varies slightly from system to system, one reasonably skilled in the art can isolate the above two compounds from a $C_{18}$ HPLC column, by eluting the two compounds in a fashion similar to that described above.

Another embodiment of the invention is directed to an isolated and purified compound derived from an extract of *Zea mays* having a molecular weight of 348 amu. In a preferred embodiment, the extract is derived from *Zea mays* corn cob using a polar solvent according to the process of the present invention, and as described in more detail in the examples which follow.

Another embodiment of the invention is directed to an isolated and purified compound derived from an extract of *Zea mays* having a molecular weight of 353 amu. In a preferred embodiment, the extract is derived from *Zea mays* corn cob using a polar solvent according to the process of the present invention, and as described in more detail in the examples which follow.

The following examples illustrate embodiments of the invention, but should not be viewed as limiting the scope of the invention.

EXAMPLES

Example 1

Effect of a Classical Phytoestrogenic Type Substance on Uterine Wet Weight.

The uterine wet weight (white bar) and DNA content (stippled bar) of ovariectomized rats housed on wood chips or in wire cages were determined and are presented in FIG. 1. There were ten animals in each group and data are plotted as the mean ±SEM for 10 experimental observations. By 14 days following ovariectomy castration, uterine wet weight (66 mg) and DNA content (460 mg) regressed to basal levels (data not shown) for the animals housed on wire. However, both uterine wet weight (95 mg) and DNA content (670 µg) were increased by nearly 45% in animals housed on the wood chip bedding. These data indicated that the wood chip bedding contained a substance with "estrogenic" activity capable of stimulating uterine hypertrophy and hyperplasia beyond that observed in the ovariectomized rats housed on wire.

Example 2

Effects of Housing Conditions on Uterine Wet Weight and DNA Content

Figure 2A:
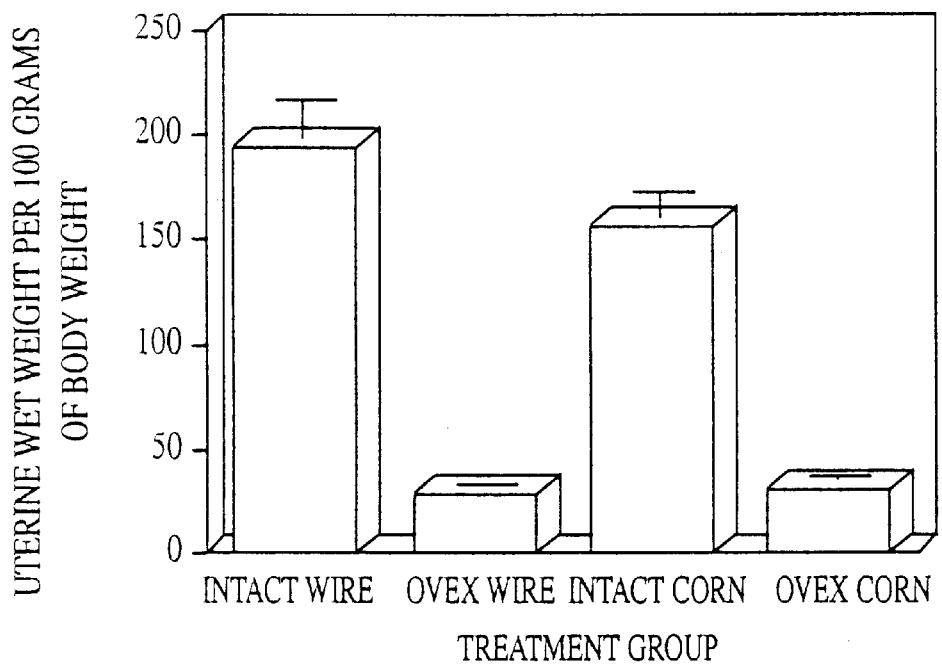
FIG. 2(A) Uterine wet weight of ovariectomized and non-ovariectomized rats housed on wire or GCCB bedding for 12 days.

To demonstrate the effects of "phytoestrogen-like substances" on the rat uterus, adult 45 day old Sprague Dawley Rats (Holtzman, Madison, Wis.) were either left with ovaries intact (INTACT) or ovariectomized (OVEX) and the animals housed for 12 days in wire cages (INTACT WIRE and OVEX WIRE) or on corn cob bedding (INTACT CORN and OVEX CORN) suspected of containing phytoestrogens. There were six animals in each of the groups. Following a 12 day period, uterine wet weight (FIG. 2A) and DNA content (FIG. 2B) were determined by standard procedures (B. M. Markaverich et al., Endocrinology. 114, 814–820, 1984; B. M. Markaverich et al. Environ. Health Perspect. 103: 574–581, 1995; M. Marcelli et al. Endocrinology 136, 1040–1048, 1995). The data in FIG. 2A demonstrate that regardless of whether the animals were housed on wire or corn cob bedding, ablation of endogenous estrogen by ovariectomy resulted in a dramatic decrease in uterine wet weight (compare INTACT WIRE to OVEX WIRE and INTACT CORN to OVEX CORN). These data suggested the ground corn cob bedding (GCCB) did not contain significant quantities of phytoestrogenic-like substances, as was the case for the wood chip bedding of Example 1 above.

Figure 2B:
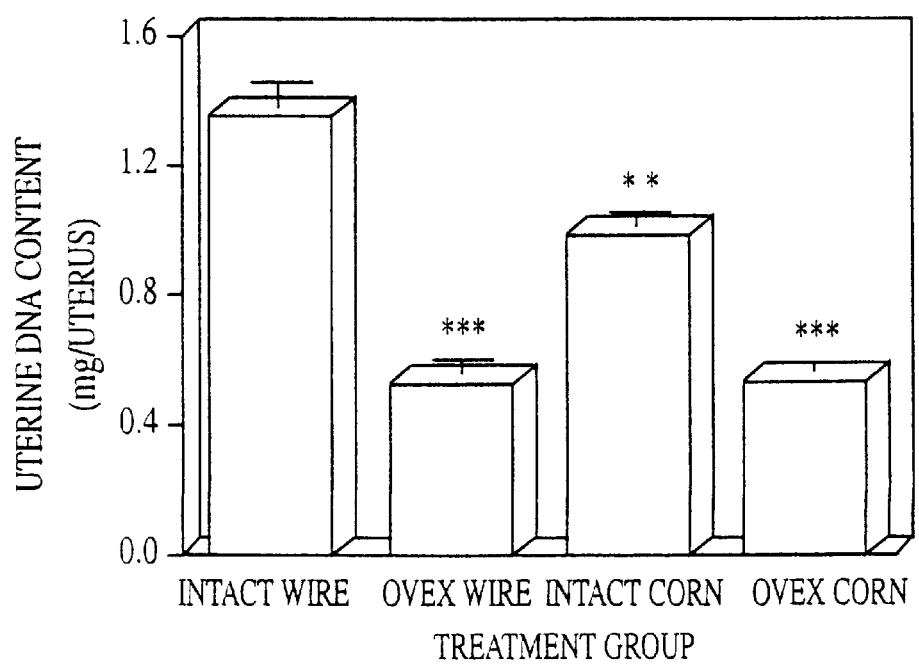
FIG. 2(B) Uterine DNA content of ovariectomized and non-ovariectomized rats housed on wire or GCCB bedding for 12 days.

Analysis of uterine DNA content from the animals in this study also supported this contention and are presented in FIG. 2B. As seen in FIG. 2B, ovariectomy resulted in a significant decrease in uterine DNA content in animals housed on wire and a more dramatic decrease was observed in the uteri from animals housed on GCCB. These finding suggested that these animals were absorbing or ingesting a component(s) from corn cob bedding with anti-estrogenic, progestational or perhaps glucocorticoid-like activity. When administered acutely, the weaker estrogens such as estriol and estradiol-17α can be antagonists of more potent estrogens such as estradiol. However, sustained exposure (as is the case for the present studies) to these impeded estrogens causes maximum uterotropic response (J. H. Clark et al., J. Steroid Biochem. 16.323–328, 1982; J. H. Clark et al., J. Steroid Biochem. 1005–1013., 1984; B. M. Markaverich et al., Endocrinology. 105: 1458–1462.1979) and can cause mammary cancer (R. L. Noble et al., Cancer Research 35, 766–780, 1975). Therefore, if the GCCB were releasing weak or impeded estrogens, sustained exposure to this bedding material should have caused hyperestrogenization of the uterus (as in Example 1) and this was not observed. These studies indicate that the "active" substance in corn cob bedding which is affecting mammalian reproduction is not a classical estrogen or phytoestrogen.

Example 3

Effects of GCCB on the Estrous Cycle of Adult Female Harlan Sprague Dawley Rats.

Figure 3:
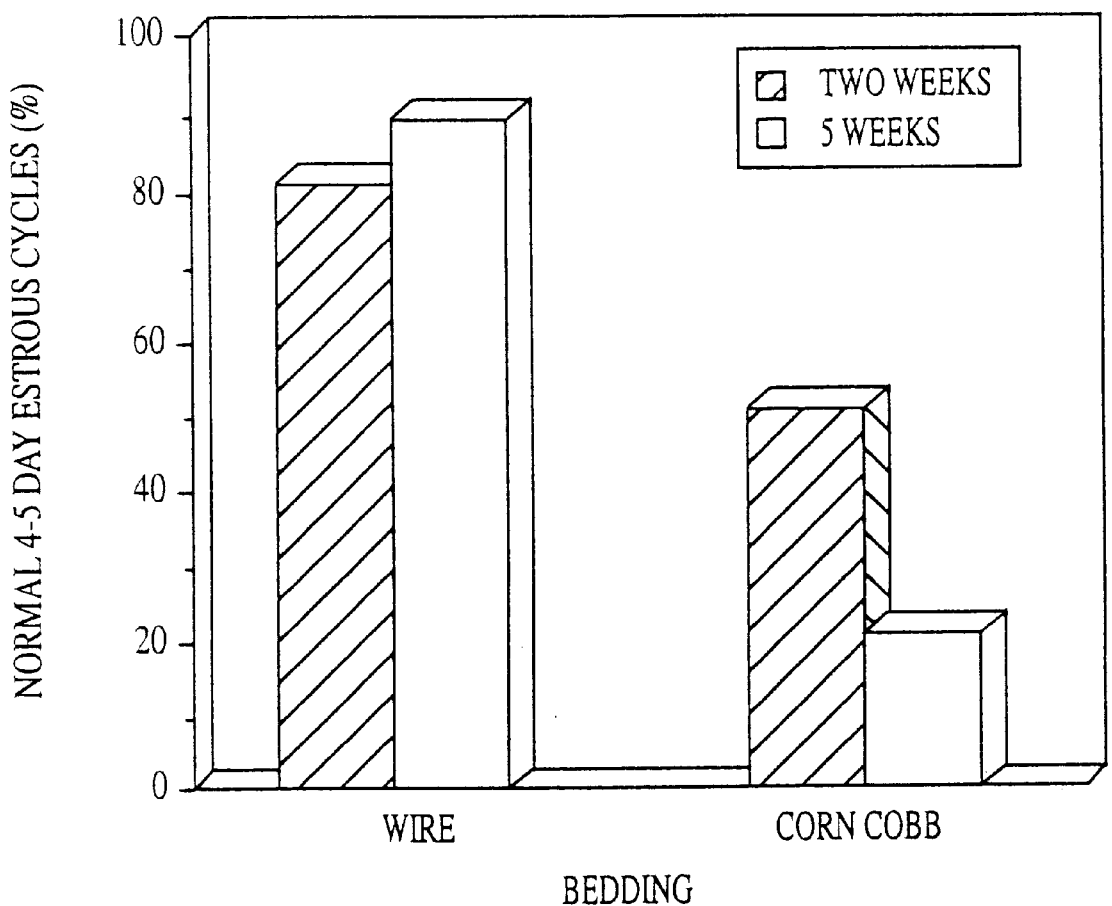
FIG. 3 Percentage of rats undergoing normal estrous cycles when housed on wire or corn cob bedding for two and five week periods.

Adult Sprague Dawley rats (5 animals per group) were housed in either wire cages or on GCCB. The estrous cycles were monitored by recording daily vaginal smears, presented in FIG. 3, for periods of up to either two (black bar) or five (white bar) weeks. 85–90% of the animals housed on wire displayed normal 4–5 day estrous cycles. Significantly, the numbers of animals that displayed normal 4–5 day cycles was decreased by 50% in the case of GCCB exposure for two weeks and by 80% in the case of GCCB exposure for five weeks compared to that of the control groups housed on wire for either two or five week periods. Careful inspection of the vaginal smears from the animals housed on GCCB indicated that the majority of these animals were in persistent metestrus which would impede breeding efficiency.

Example 4

Reversibility of the GCCB-Induced Effects on the Estrous Cycle of Adult Female Harlan Sprague Dawley Rats.

Figure 4:
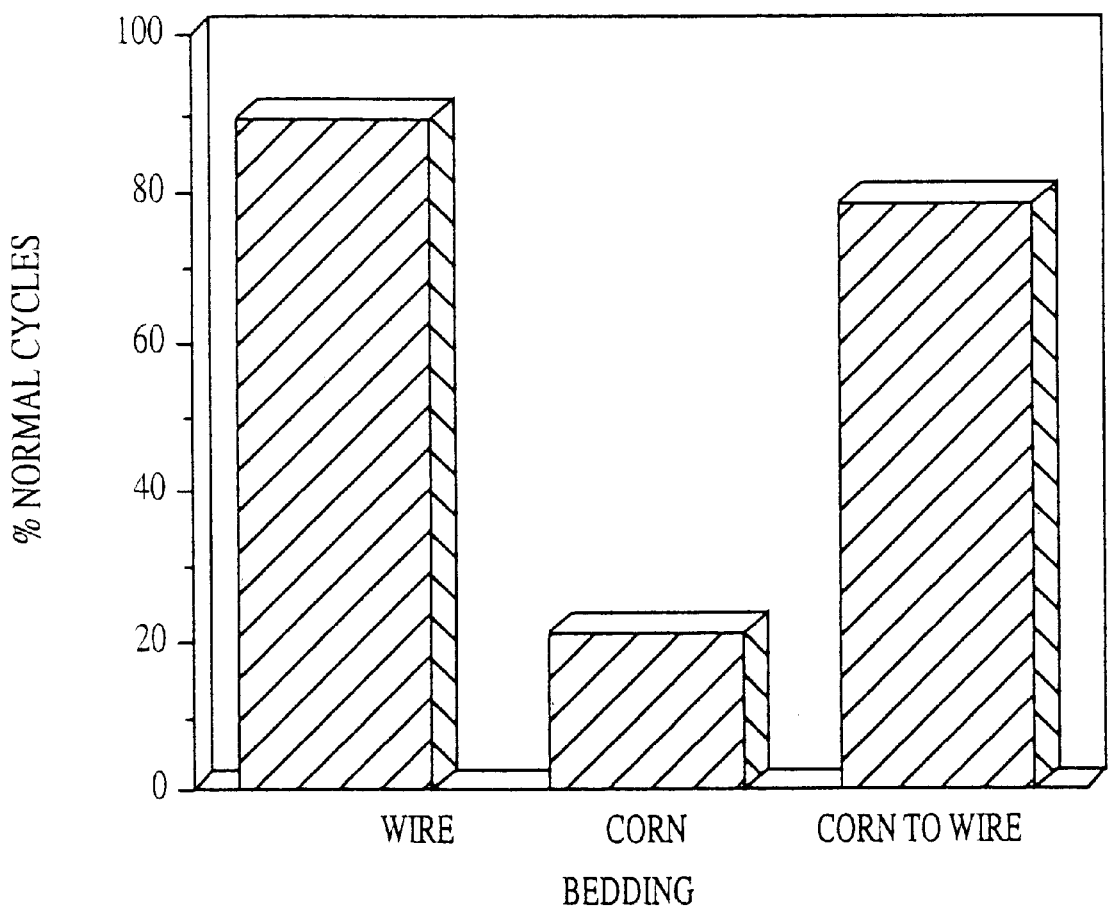
FIG. 4 Percentage of rats undergoing normal estrous cycles when housed on wire, corn cob or transferred from corn cob to wire bedding.

The data presented in FIG. 4 reveal that the effects of GCCB on the estrous cycles of adult female rats is reversible. For this study, vaginal smears were taken daily for a group of ten adult Harlan Sprague Dawley rats that were housed first in wire cages for 14 days (WIRE), transferred to GCCB for 14 days (CORN) and then returned to wire cages for 14 more days (CORN TO WIRE). The numbers of animals displaying normal 4–5 day estrous cycles reveal that the effects of corn cob bedding on the estrous cycles of these animals was reversible. Again, careful inspection of the vaginal smears from the animals housed on GCCB indicated that the majority of these animals were in persistent metestrus which would impede breeding efficiency.

Example 5

Effects of GCCB on Estrogen Receptor and Type II binding sites.

Figure 6A:
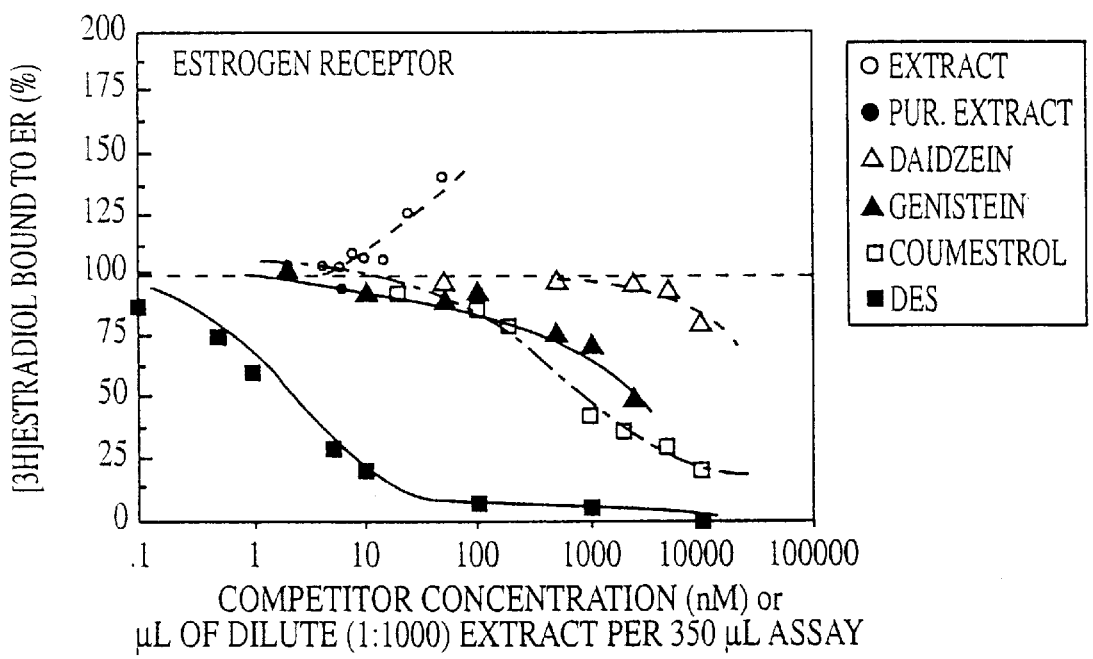
FIG. 6(A) Effects of corn cob extracts on estrogen receptor binding by estradiol.
Figure 6B:
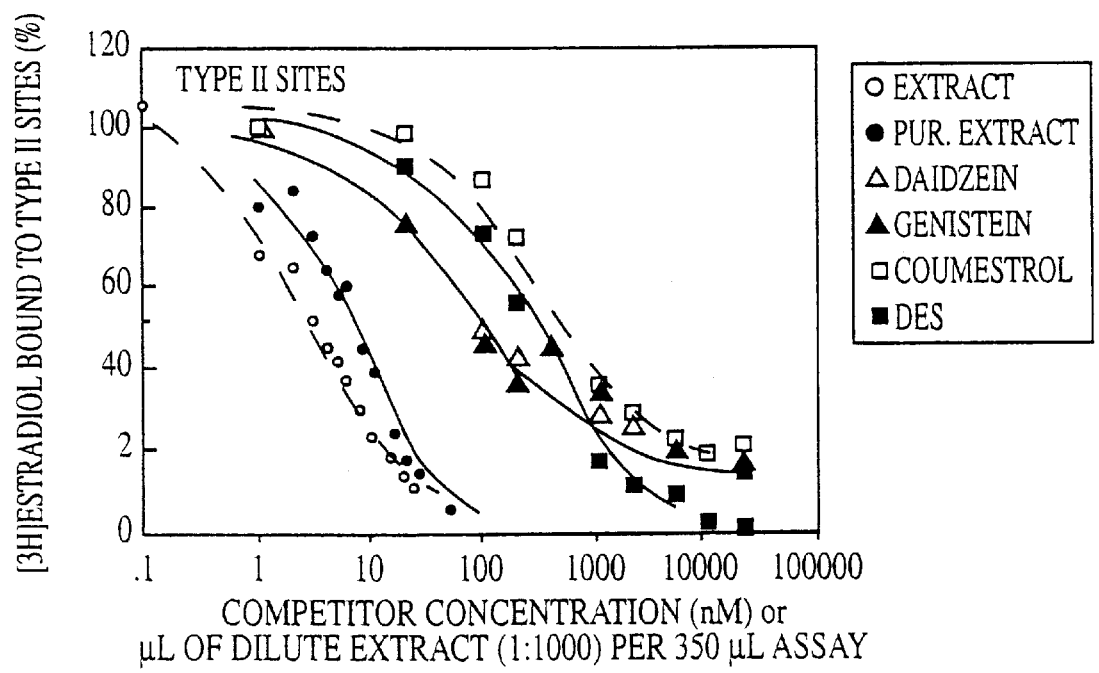
FIG. 6(B) Effects of corn cob extracts on Type II site binding by estradiol.

The effects of GCCB on estrogen receptor binding sites and Type II receptor binding sites were assessed. The results of the analysis are shown in FIGS. 6A and 6B. Briefly, cytosolic fractions (FIG. 6A, estrogen receptors) or nuclear fractions (FIG. 6B, Type II sites) were prepared by standard procedures. GCCB was extracted with methanol, dried under nitrogen and resolubilized (1:1000) in 10% ethanol in 10 mM Tris, 1 mM EDTA buffer (crude extract). Alternatively, the 80% methanol in water eluate of an aliquot of GCCB extract was purified via chromatography on a Spice $C_{18}$ cartridge (Pur. Extract, closed circles) dried and also rediluted (1:1000) in 10 mM Tris, 1 mM EDTA 10% ethanol buffer. Aliquots of the rediluted extract (1–50 µl), ethanol-TE buffer vehicle only (Control) or the indicated concentration of the estradiol competitors diethylstilbestrol (DES, closed squares), daidzein (open triangles), genistein (closed triangles), or coumestrol (open squares) were added to cytosolic (ER) or nuclear preparations (Type II sites) containing [$^3$H] estradiol (10 nM for estrogen receptor; 30 nM for Type II) and binding to estrogen receptor or Type II sites was determined by the method of Markaverich et al. (Environ. Health Perspect. 103: 574–581, 1995; Endocrinology 109: 62–69, 1981).

The results demonstrate that unlike classical phytoestrogens such as daidzein, genistein, and coumestrol, which competitively inhibit [3H] estradiol binding to the estrogen receptor (FIG. 6A), neither the crude nor purified corn bedding extract competed for ER binding in rat uterine cytosol over the limited solubility range used. The results suggest that these GCCB extracts do not contain significant quantities of a compound which interacts with the hormone binding domain of the estrogen receptor.

Example 6

Effects of GCCB on Female and Male Sexual Behavior.

Figure 5A:
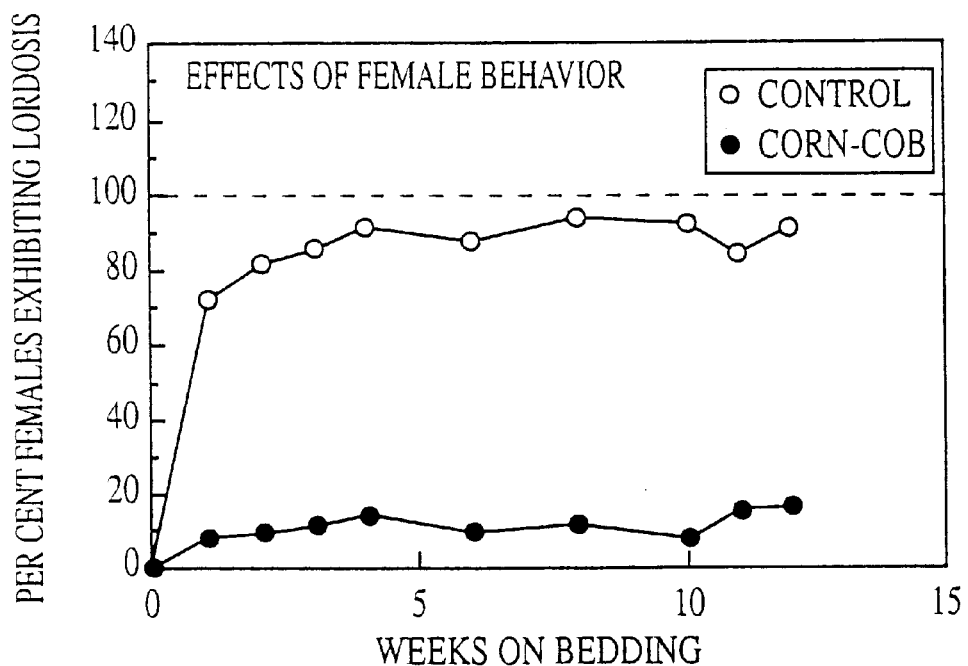
FIG. 5(A) Effects of housing conditions on female sexual behavior.
Figure 5B:
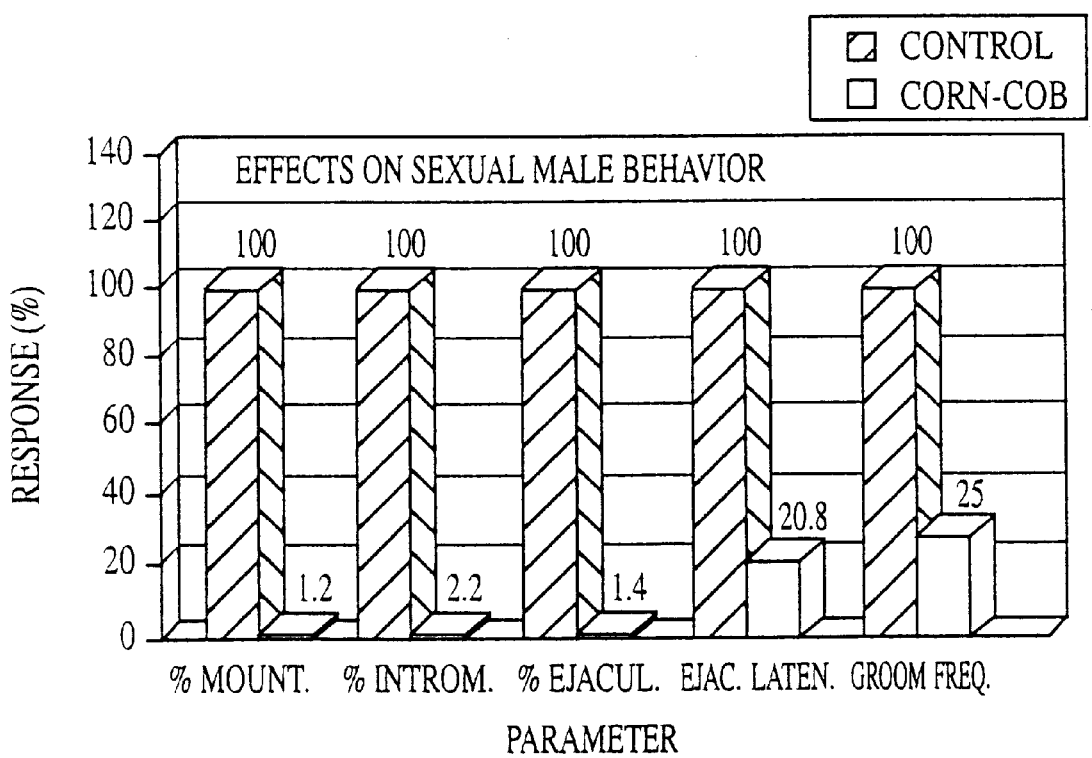
FIG. 5(B) Effects of housing conditions on male sexual behavior.

Exposure to GCCB also had significant effects on male and female mating behavior, shown in FIGS. 5A and 5B. Briefly, ovariectomized female rats were primed subcutaneously with 2 μg of estradiol benzoate in sesame oil. Forty-eight hours later they were administered 100 μg of progesterone subcutaneously. Four hours after progesterone administration, their sexual behavior was analyzed in the presence of male proven breeder rats. Sexual behavior was scored and quantitated as lordosis response. The females were on Sani-chip bedding (control) or on GCCB (corn-cob). The results are presented in FIG. 5A.

Adult male proven breeders were placed in individual cages on Sani-chip bedding (control, open circles) or GCCB (corn-cob, closed circles) and their sexual performance evaluated in the presence of sexually receptive ovariectomized, hormone-treated female rats. Male sexual behavior was evaluated by examining number of mounts, intromissions, ejaculations, ejaculation latencies (in seconds) and grooming frequencies in a 30-minute test period with each sexually receptive female. The results are listed in FIG. 5B.

When female mating behavior of rats housed on GCCB was monitored for over 11 weeks, only 10–15% of the animals displayed lordosis as compared to the Sani-chip controls (FIG. 5A). Similarly, housing of male animals on GCCB significantly blocked male sexual behavior (FIG. 5B). Mounting, intromission and ejaculation efficiencies were decreased by nearly 99% in GCCB housed males relative to Sani-chip controls. Ejaculation latency and grooming frequency were also decreased by 75–80% in animals housed on GCCB (FIG. 5B). These observations demonstrate that GCCB contains an activity which is capable of affecting male and female reproductive function.

Example 7
Extraction of Corn Cob and GCCB.

GCCB, fresh corn, kernels, and cobs were extracted separately in 100% methanol at 70° C. for 2 hours. The extracts were dried under vacuum at 70° C. and redissolved in dimethyl sulfoxide (DMSO). Aliquots of the redissolved extract (2, 5 or 10 μl) were added to cultured MCF-7 human breast cancer cells.

Example 8
Isolation of a Mitogenic Activity from GCCB Extract.

An aliquot of the GCCB crude extract was fractionated on a Spice $C_{18}$ Cartridge (a reverse phase column using aliphatic groups attached to a matrix to form a hydrophobic adsorbent. Rainin Instruments Company). Briefly, a GCCB extract in 20% methanol in water was loaded onto a spice cartridge and the pass through (20% methanol) fraction was collected. The column was sequentially eluted with a solution of water comprising 40%, 60%, and 80% methanol in water. The final elution was with 100% methanol. Each fraction, including the pass through fraction, was collected and dried at 50° C. under nitrogen to remove methanol. The eluate was re-dissolved in 100% ethanol. Aliquots of each fraction were added to cultures of MCF-7 (ER+) or MDA-231 (ER-) human breast cancer cells grown in phenol red free medium. Control wells received only the ethanol vehicle. Twenty-four hours after plating the cells, the media was changed and the cells were treated with various doses of GCCB extract (2–10 ml) alone, or in combination with 10 nM estradiol. Compounds were added to the media in ethanol and ethanol concentration was maintained at 0.2% in all wells including controls. Six days following treatment, cell number was determined by hemocytometer counts and results are expressed as cell number in treated wells relative to ethanol controls (100%) as described (B. M. Markaverich et al., J. Steroid Biochem. 29:71–78, 1988; B. M. Markaverich et al., Cancer Res. 50: 1470–1478, 1990; B. M. Markaverich et al., JBC 263: 7203–7210, 1988; B. M. Markaverich et al., Internat. J. Oncol. 4:1291–1300, 1994).

Figure 7:
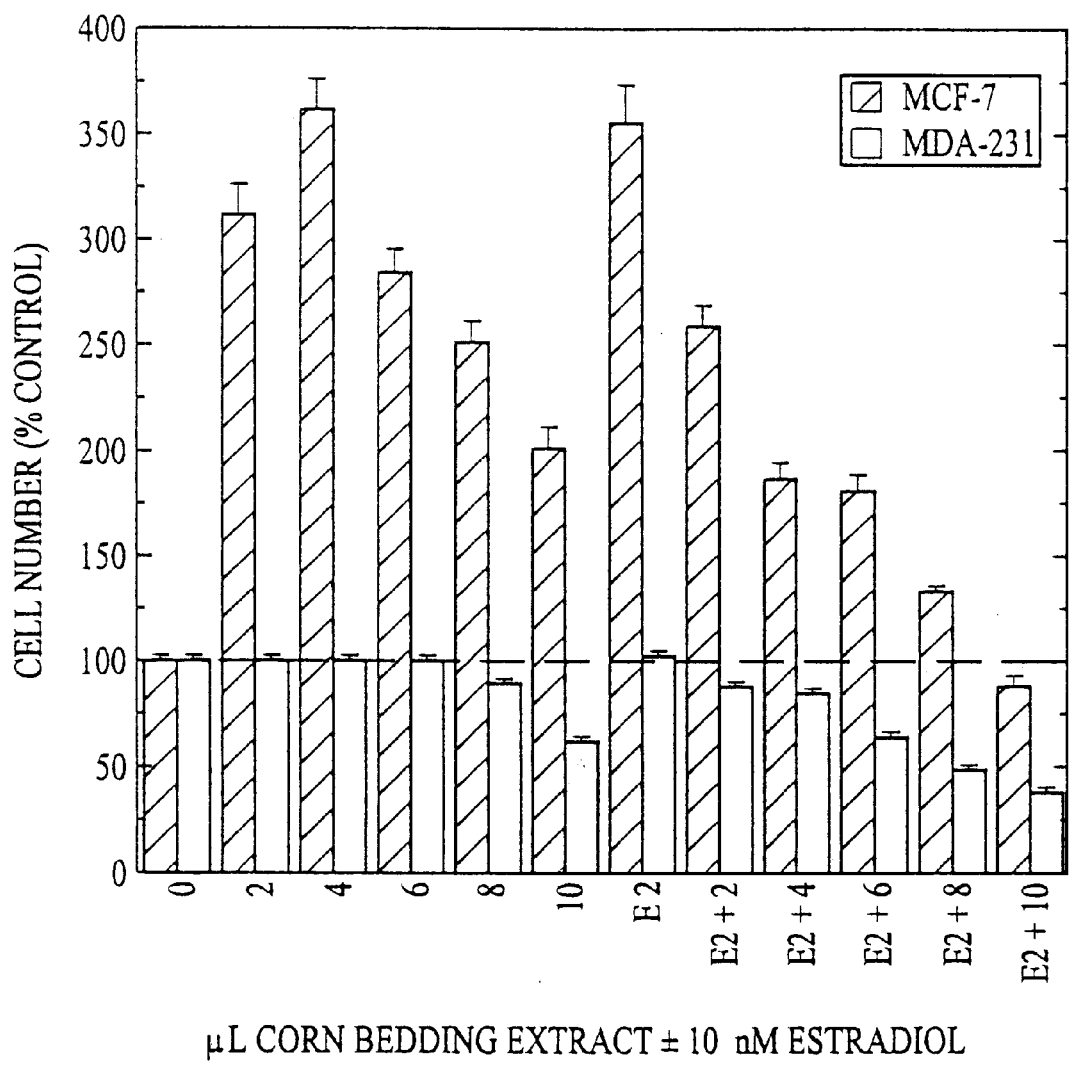
FIG. 7 Effects of corn cob extract and estradiol on cell growth.

The results of this study are shown in FIG. 7. The crude extract stimulated the proliferation of MCF-7 cells (black bars), but not MDA-231 cells (white bars). All of the mitogenic activity was recovered in the 80% methanol in water eluate from the Spice $C_{18}$ cartridge. The observation that the corn cob bedding extract failed to stimulate the proliferation of ER-negative MDA-231 human breast cancer cells is of interest. At higher concentrations, in the presence or absence or estradiol, corn cob extract inhibited growth of MDA-231 cells. The differential response of MCF-7 and MDA-231 cells to corn cob extract suggests that the ER-regulated pathways are at least peripherally involved in the mechanism through which the active component in the corn cob extract stimulates MCF-7 cell proliferation.

Figure 8:
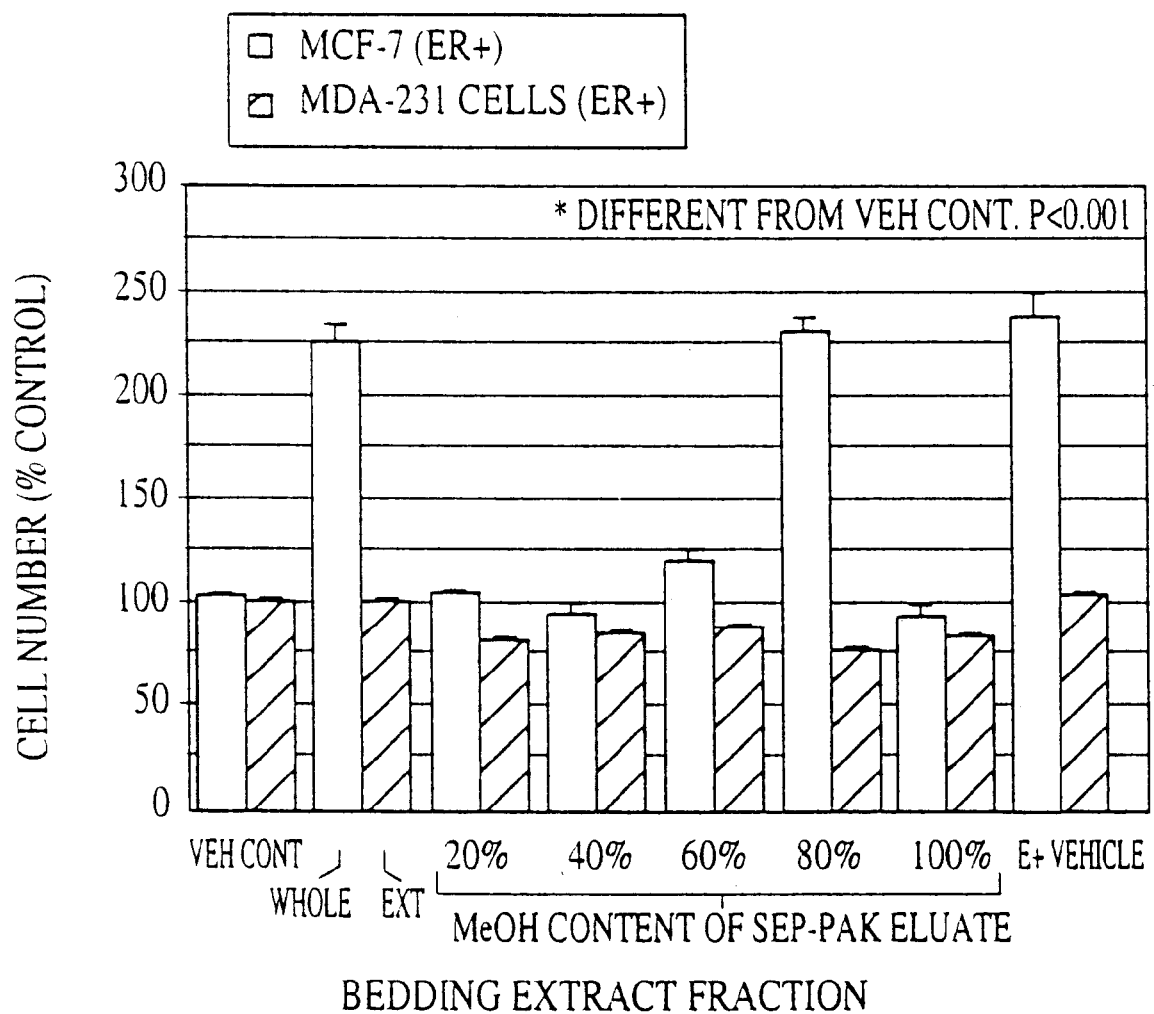
FIG. 8 Effects of corn cob extract column fractions on cell growth.

In a further study, the effects of fractionated GCCB extract on the proliferation of the MCF-7 and MDA-231 human breast cancer cells were analyzed. Briefly, a crude GCCB extract was prepared as described above and diluted 1:1000 in TE methanol and fractionated on a Spice $C_{18}$ cartridge. Briefly, fractionation was accomplished by loading the extract (2 ml) onto the column and collecting the pass through (20% methanol in water) fraction. The column was then successively eluted with 2 ml volumes of 40%, 60%, 80% methanol in water solutions. Final elution was with 100% methanol. Each of these fractions were collected for assay. Aliquots of the crude extract (Whole Ext) and the 20%, 40%, 60%, 80% and 100% methanol cartridge eluates were taken to dryness at 50° C. under nitrogen, redissolved in 500 μl of ethanol and 20 μl aliquots were added to the cells 24 hours following plating (Day 0). Six days following treatment, cell number (% Control) was determined. Data represent the mean SEM and were analyzed statistically via ANOVA and Tukeys test on the means using Instat. As can be seen in FIG. 8, the response of MCF-7 cells (black bars) to the purified material (80% methanol fraction) was equivalent to that obtained with the crude extract or estradiol.

Experimental studies were performed to determine if GCCB extract has an effect on [$^3$H]estradiol binding to estrogen receptor or nuclear Type H sites in rat uterine preparations. Cytosolic and nuclear fractions were prepared by standard procedures (B. M. Markaverich et al., Environ. Health Perspect. 103: 574–581, 1995; M. Marcelli et al. Endocrinology 136, 1040–1048, 1995). GCCB was extracted with methanol, and the crude extract dried under nitrogen and rediluted (1:1000) in 100% ethanol in TE buffer (crude extract). Alternatively, the 80% methanol in water eluate of an aliquot of GCCB extract was purified via chromatography on a Spice $C_{18}$ Cartridge (Pur. Extract), dried and also rediluted (1:1000) TE-10% ethanol buffer. Aliquots of the rediluted extract (1–50 μl), ethanol-TE buffer vehicle (control) or the indicated concentrations of diethylstilbestrol (DES), daidzein, genistein, or coumestrol were added to the cytosolic (estrogen receptor) or nuclear preparations (Type II sites) containing [$^3$H]estradiol (10 nM for estrogen receptor, 30 nM for Type II) and binding to estrogen receptor or Type II sites was determined by well documented procedures (Markaverich, B. M. et al. Environ. Health Perspect. 103: 574–581, 1995; B. M. Markaverich et. al. Endocrinology. 109: 62–69, 1981). As seen in FIG. 6, GCCB extract competed for [$^3$H]esatradiol binding to nuclear Type II sites, but not to estrogen receptors.

Figure 9:
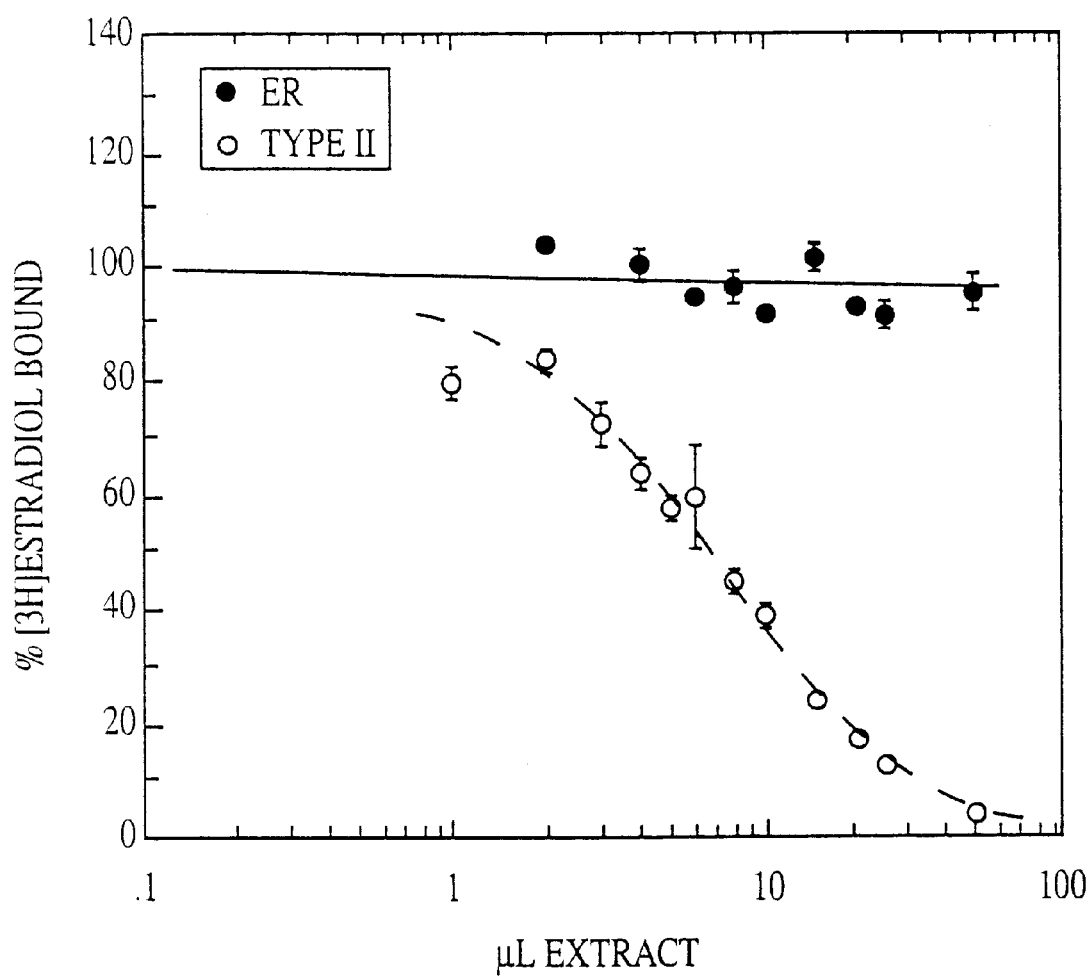
FIG. 9 Effects of corn cob extract on estrogen receptor binding and Type II site binding by estradiol.
Figure 10:
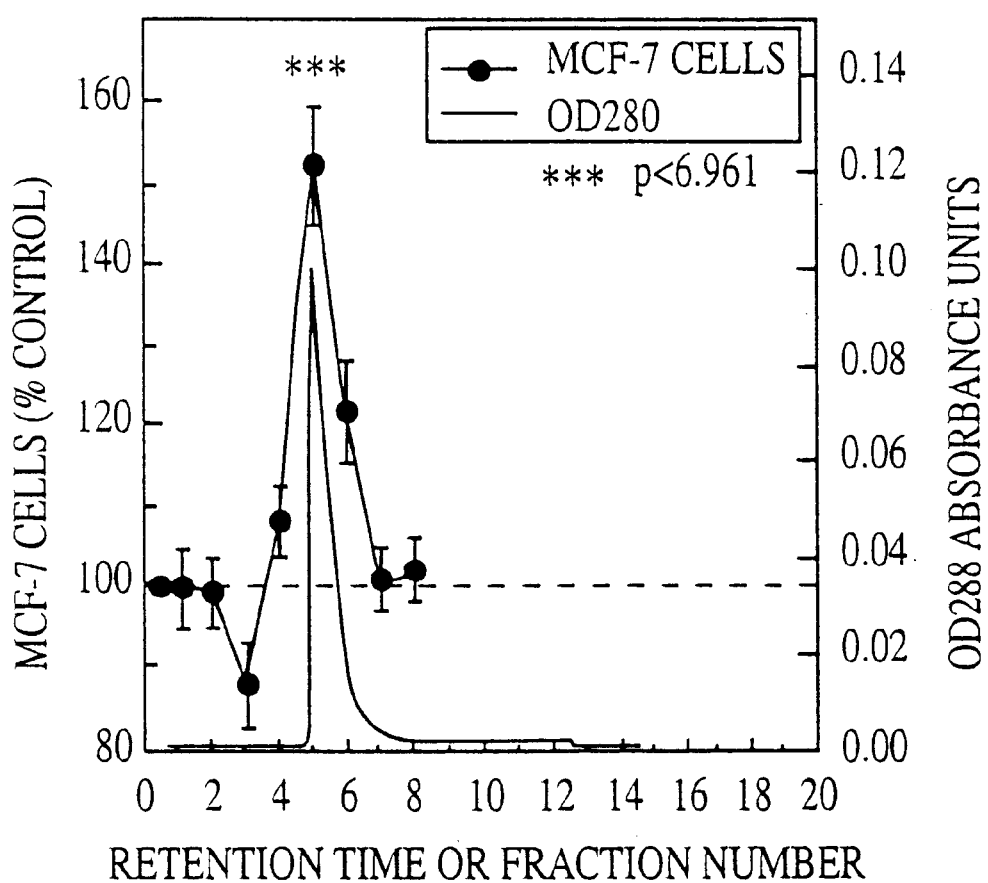
FIG. 10 Effects of corn cob extract column fractions on cell growth.

Further characterization of the 80% methanol eluate from the Spice cartridge by HPLC revealed that the GCCB extract eluted from a Waters micro-bondapack $C_{18}$ column as a single major peak of UV absorbing material. Fractions were collected as indicated in the chromatogram and aliquots were added to MCF-7 human breast cancer cell cultures. The mitogenic activity in GCCB extract eluted from a $C_{18}$ Sephadex column as a single, major component. The data in FIG. 10 demonstrate that a single peak of mitogenic activity eluted from the column together with a peak of UV absorbing material. The symmetry of the HPLC peak suggests that this material has been purified to near homogeneity and that the compound of FIG. 9 shown to interact with Type II sites is likely to be responsible for stimulating MCF-7 human breast cancer cell proliferation. This stimulation was not observed in MDA-231 cells and, in fact, the preparations partially inhibited MDA-231 cell proliferation. This is similar to the results achieved with partially purified preparations and the HPLC purified material, shown in FIGS. 7 and 8.

Example 9
Effects of Cob Bedding Extract on ER-Mediated Gene Transcription.

The effect of purified ground corn cob bedding extract on estrogen mediated gene transcription in mammalian cells was determined using HeLa cells lacking endogenous estrogen receptors (ER). The ER-negative HeLa cells were co-transfected with the construct psvmt:wE, which encodes for exogenous estrogen receptor, the construct pERE-E1b-LUC, which contains an estrogen responsive element (ERE) regulating the expression of the luciferase reporter gene and the construct pCMVpgal, which encodes a housekeeping gene to assess basal levels of gene expression in these cells. Expression of pCMVβgal was used for normalization of the response of the pERE-E1b-LUC reporter construct to estradiol and the ground corn cob bedding extract.

Figure 11:
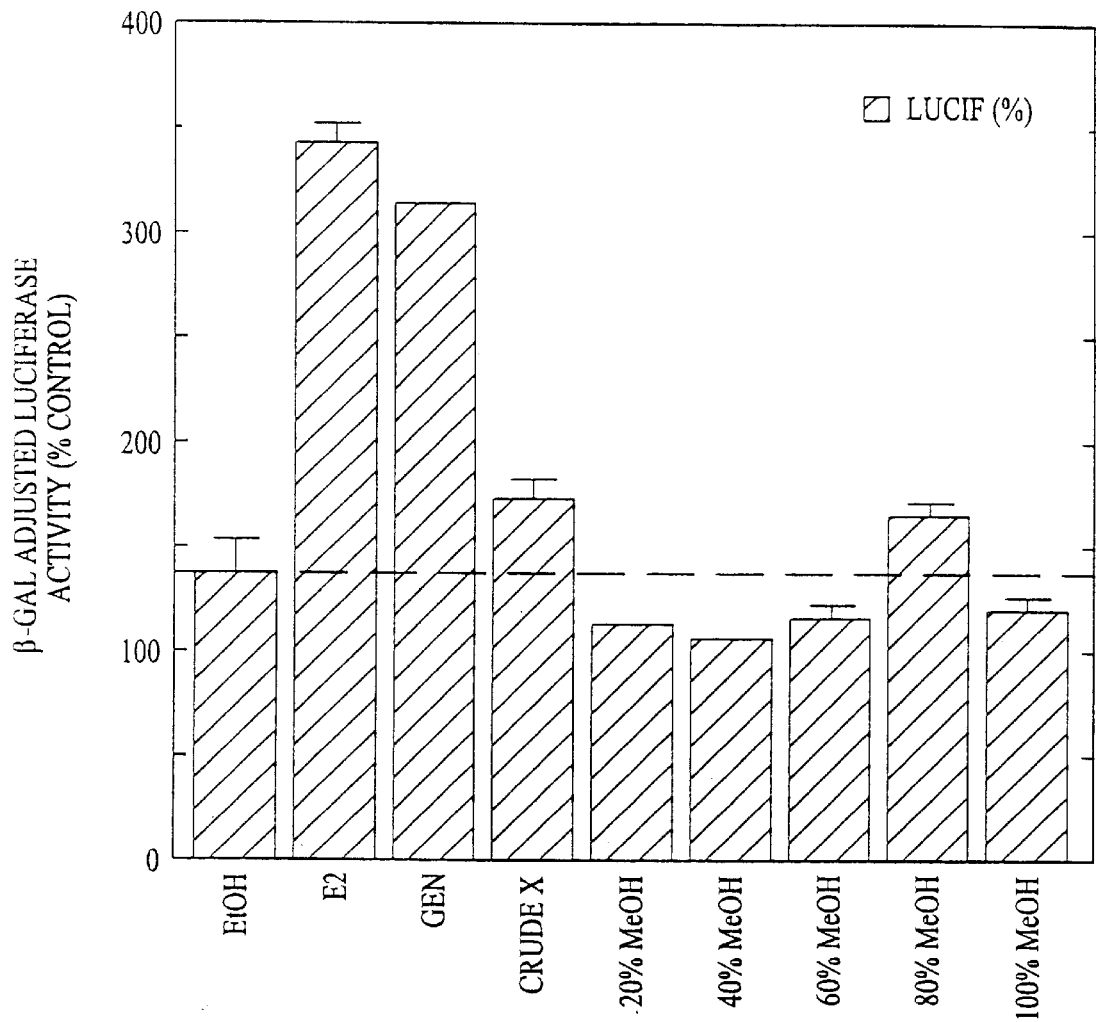
FIG. 11 Effects of ground corn cob bedding extract on estrogen receptor-mediated gene transcription.

As shown in FIG. 11, treatment of HeLa cells with either 1 nM estradiol ($E_2$) or 10 nM of the phytoestrogen genistein (GEN) resulted in a stimulation of ER-mediated luciferase activity greater than two fold of that of the control (EtOH). Treatment of the transfected cells with either a crude ground corn cob bedding extract (CRUDE X) or purified ground corn cob bedding fractions eluting from Spice $C_{18}$ Cartridges (20%, 40%, 60%, 80% or 100% methanol eluates) failed to significantly stimulate the activity of the reporter transgene relative to the control. These data indicate that it is unlikely that a component in the ground corn cob bedding extract affects transcription via direct binding interactions with the estrogen receptor or through an estrogen-responsive signal transduction pathway.

Example 10
Effects of Anti-estrogen, Estrogen or Corn Cob Bedding Extract Stimulation of MCF-7 Cells.

Experimental studies were performed to assess the ability of a pure anti-estrogen (ICI-182,780) to effect the ability of the ground corn cob bedding extract to stimulate MCF-7 human breast cancer cell proliferation. It is known that antiestrogen ICI-182,780 blocks cellular proliferation at the level of the estrogen receptor. If the ability of the ground corn cob bedding extract to stimulate MCF-7 cell proliferation (see FIGS. 7, 8 and 10) is mediated via direct interaction with the estrogen receptor or through an estrogen-responsive signal transduction pathway, then one would predict that ICI-182,780 would block this corn cob extract-dependent proliferative response of MCF-7 cells.

Figure 12:
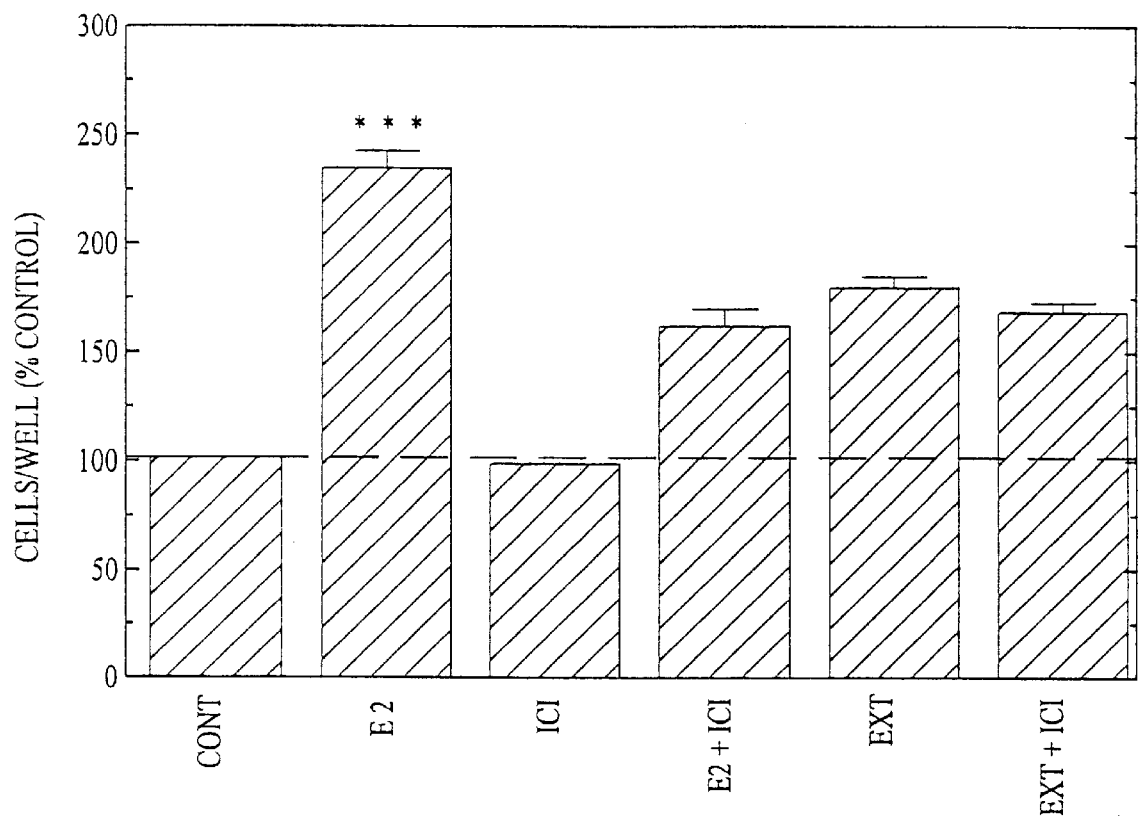
FIG. 12 Effects of antiestrogen on the stimulation of cell proliferation by estrogen or the purified corn cob bedding extract.

Exponentially growing cultures of MCF-7 cells were treated with 1 nM estradiol ($E_2$), 10 nM ICI-182,780 (ICI) or 10 μl of the highly purified ground corn cob bedding extract (80% eluate from Spice $C_{18}$ Cartridge) alone or in combination. Cell number was determined 6 days following treatment. As shown in FIG. 12, E2 treatment resulted in a 2–3 fold stimulation of MCF-7 cell proliferation relative to control (CONT). Although ICI-182,780 (ICI) alone failed to inhibit the proliferation of these cells in the absence of estrogen, antagonistic activity of ICI-182,780 was observed when it was added to cells stimulated with E2 (compare $E_2$ versus ICI versus $E_2$ +ICI treatment groups). The ICI antiestrogen blocked greater than 50% of the estradiol-induced stimulation of MCF-7 breast cancer cell proliferation.

In addition, the purified ground corn cob bedding extract (EXT) alone stimulated MCF-7 cell proliferation (FIG. 12) and this response was not blocked by the antiestrogen (compare EXT group to ICI+EXT group). These data suggest that the active mitogen in the ground corn cob bedding extract is not a typical phytoestrogen, mycotoxin or xenobiotic which controls cellular proliferation via direct interaction with the estrogen receptor. Thus, the mitogenic agent in ground corn cob bedding may control cellular growth and proliferation by a previously unknown mechanism.

Example 11
Effects of Highly Purified Corn Cob Bedding Extract on the Estrous Cycle.

Experimental studies were performed to determine if the material isolated from the highly purified corn cob bedding extract is responsible for the disruption of normal estrous cycles in animals. Ground corn cob was extracted as described in Example 8. The extract was purified by chromatography on Spice $C_{18}$ cartridges. The 80% methanol eluate was examined to determine whether it had biological activity in animal studies.

Figure 13:
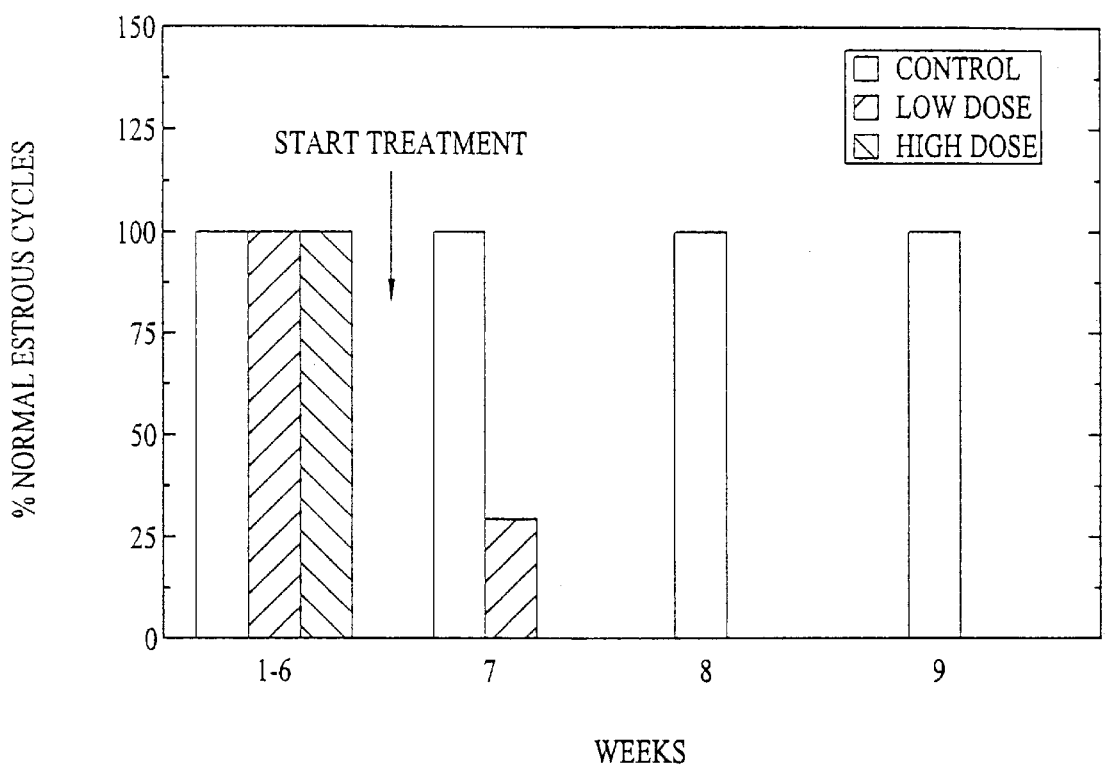
FIG. 13 Effects of various doses of corn cob extract on rat estrous cycles.

Thirty adult female rats housed in wire cages were divided into three treatment groups (controls, low dose extract and high dose extract groups) of ten rats each. Food and water were provided ad libitum and the estrous cycles of these animals were followed by monitoring daily vaginal smears for 6 weeks. The low dose group was fed 50 μl of the 80% methanol eluate per 400 ml drinking water. The high dose group was fed 100 μl of the 80% methanol eluate per 400 ml of drinking water. As shown in FIG. 13, the results of the study demonstrate that animals in all three groups have normal 4–5 day estrous cycles for the initial 6 weeks of the study.

At the end of the sixth week, the animals in these three groups were given either a low dose (400 μl corn cob extract per 400 ml water) or high dose (2000 μl extract per 400 ml water) of ground corn cob bedding extract in the drinking water or water only (controls) and fluid consumption was monitored twice weekly throughout the study. The methanol solvent in the corn cob extract was replaced with ethanol. Aliquots of the 80% methanol extract were dried under nitrogen, redissolved in equal volumes of 100% ethanol and added to the drinking water in this vehicle. To control for any ethanol-dependent effects, a volume of ethanol equivalent to the high dose (2000 μl per 400 ml of drinking water) was also added to the drinking water as control. No effects on body weights, fluid consumption or estrous cycle duration were noted as a result of treatment with the ethanol vehicle control.

Daily vaginal smears were collected from animals in all three groups for an additional 3 weeks. The data clearly show that 70% of the animals receiving the low dose ground corn cob bedding extract displayed abnormal estrous cycles following I week of treatment and 100% of these animals were acyclic by 2 or 3 weeks following treatment. A more pronounced effect was observed with the high dose of ground corn cob bedding extract where 100% of the animals were acyclic during all three weeks of the treatment period.

These data demonstrate that the highly purified ground corn cob bedding extract contains a substance(s) which interrupts normal cyclicity in female rats.

Example 12
High Performance Liquid Chromatography of GCCB Extract.

An aliquot of the 80% methanol fraction of GCCB extract was injected onto a $C_{18}$ (Waters micro-bondapak) reversed phase column eluted with 70% methanol in water at a flow rate of one ml per minute. One ml fractions were collected (one each minute) and taken to dryness under nitrogen at 50° C., resuspended in 10 μl of 100% ethanol. The fractions were added to exponentially growing MCF-7 cells and also the $O.D._{280}$ absorbance was determined for each fraction. Cell number was determined 6 days following treatment and data are presented in FIG. 10 as the mean ±the SEM for twelve determinations. The cell number determined for each fraction (% Control) is shown plotted over the $O.D._{280}$ absorbance tracing representing the chromatogram. The data reveal that a single peak of MCF-7 stimulating activity (closed circles) eluted from the column together with a single peak of UV absorbing material. Thus, the UV absorption activity co-elutes with cell proliferation stimulating activity.

Example 13
Effects of Purified GCCB Extract on [$^3$H]estradiol Binding to Estrogen Receptor or Nuclear Type II Sites.

Rat uterine cytosolic fractions (estrogen receptor) and nuclear fractions (Type II sites) were prepared as follows. The 80% methanol in water eluate of an aliquot of GCCB extract purified via chromatography on a Spice $C_{18}$ Cartridge was dried and rediluted (1:1000) TE-10% ethanol buffer. Aliquots of the rediluted extract (1–50 μl) in ethanol-TE buffer vehicle (control) were added to the cytosolic and nuclear fractions containing [$^3$H]estradiol (10 nM for estrogen receptor, 30 nM for Type II sites) and binding to estrogen receptor (ER) or Type II sites (TYPE II) was determined by well documented procedures (B. M. Markaverich et al. Environ. Health Perspect. 103: 574–581, 1995; B. M. Markaverich et. al. Endocrinology 109: 62–69, 1981). The results in FIG. 9 show that highly purified GCCB extract preparations competed for [$^3$H]estradiol binding to nuclear Type 11 sites, but did not compete for binding to the estrogen receptor.

Example 14
Effects of diluted Extract on Estrogen Receptor Negative Cells.

Figure 14:
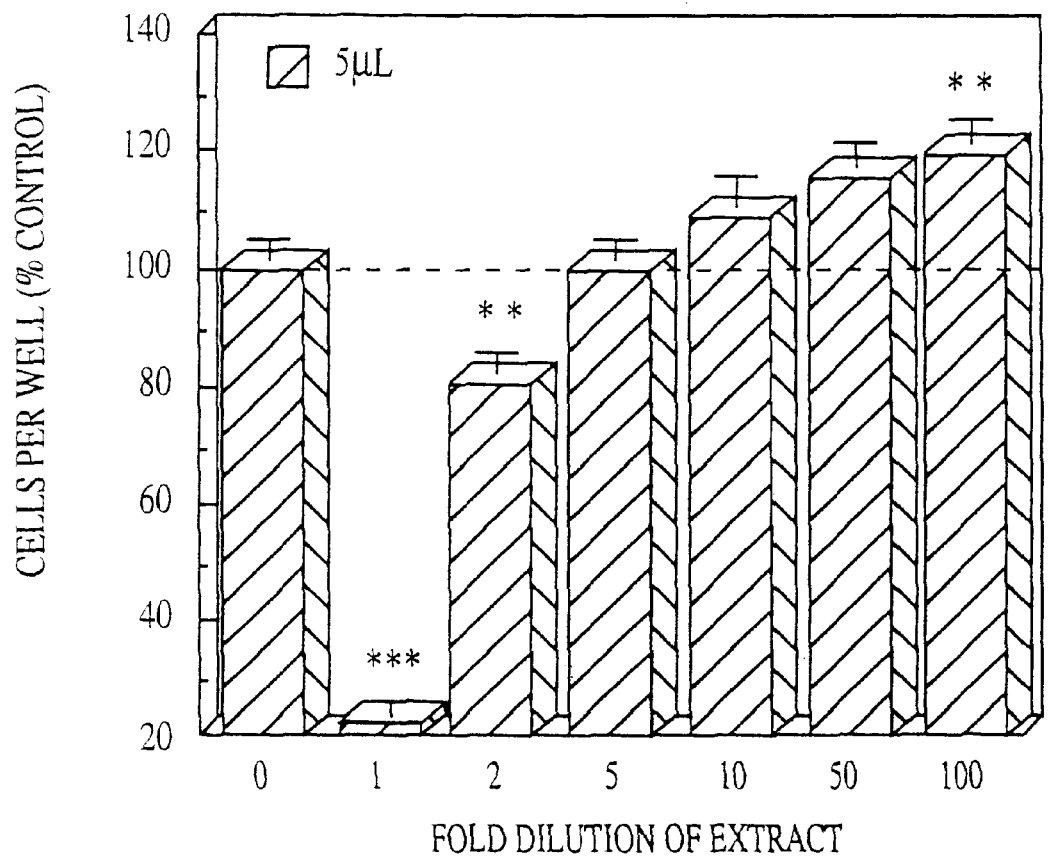
FIG. 14 Effects of diluted corn cob extract on cells lacking estrogen receptors.

Experimental studies were performed to determine if the corn cob extract at a more dilute concentration comprises mitogenic activity. It is possible that MDA-231 cells are not stimulated by the corn cob bedding because they may be more sensitive to the mitogenic agent than are MCF-7 cells. Shown in FIG. 14, 5 ml of various dilutions (1, 2, 5, 10, 50 and 100 fold dilutions) of corn cob extract were added to exponentially growing MDA-23 1 cells. Cell number was determined by hemocytometer counting 11 days following treatment. The bar denoted 0 is data from MDA-231 cells treated with 5 ml of the ethanol vehicle as a control. While concentrated preparations of the corn cob extract inhibited MDA-231 cell proliferation, cell stimulation became apparent as the corn cob extract was diluted (compare 10, 50 and 100 fold dilutions with the 1, 2 and 5 fold dilutions).

Figure 15:
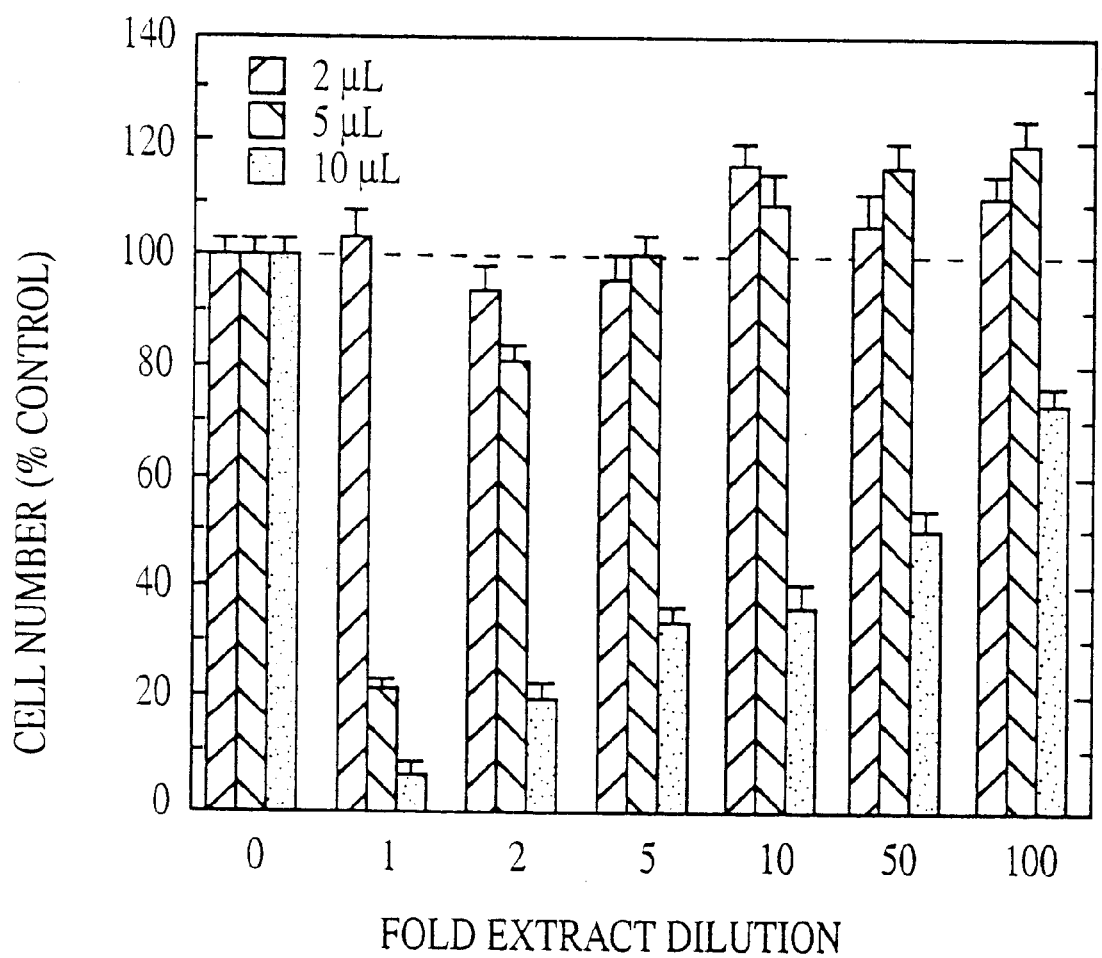
FIG. 15 Effects of various concentrations of diluted corn cob bedding extract on proliferation of cells lacking estrogen receptors.

In a separate experiment, exponentially growing MDA-23 1 cells were treated with 2 ul (grey bars), 5 ul (black bars), 10 μl (striped bars) of the indicated dilution (1, 2, 5, 10, 50 and 100 fold) of a corn cob bedding extract in ethanol or ethanol vehicle only as a control (bar labeled 0). Cell number was determined by hemocytometer counting 11 days following treatment. As seen in FIG. 15, 2 μl and 5 pi of a 10 fold, 50 fold, or 100 fold dilution of corn cob extract stimulated the proliferation of MDA-231 human breast cancer cells. These data clearly indicate that MDA-231 cell growth inhibition is observed with higher concentrations of these extracts and mitogenic activity is observed with lower concentrations of the extract.

Example 15
Effects of Methotrexate and GCCB Extracts on Breast Cancer Cells.

Figure 16:
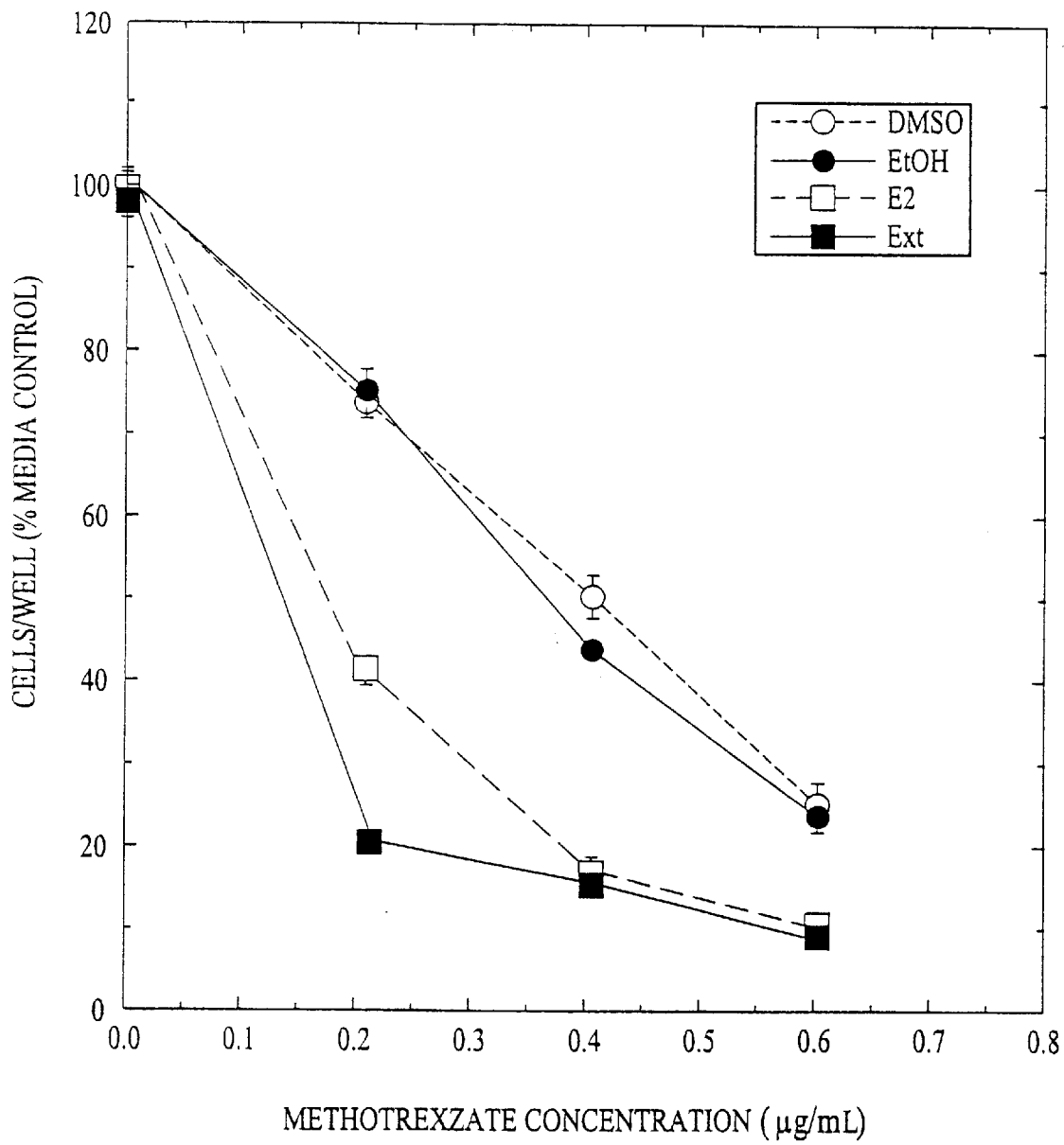
FIG. 16 Bedding extract effects on Methotrexate inhibition of MCF-7 breast cancer cells.

Exponentially growing MCF-7 human breast cancer cells were treated with Methotrexate alone (open and closed circles), Methotrexate and estradiol (E2, open squares), or a combination of Methotrexate and purified corn cob bedding extract (Ext, closed squares). Cell number was determined 11 days following treatment. Vehicle controls (DMSO, open circles and ethanol, closed circles) were added to the Methotrexate alone in order to control for any vehicle-dependent effects in the experiment. The experimental data are shown in FIG. 16. The combination of Methotrexate and corn cob extract suppressed the proliferation of MCF-7 cells more effectively than Methotrexate and estradiol.

Example 16
Effects of Fresh Corn Extract on Cell Growth.

Fresh corn on the cob was purchased at a local supermarket and the kernels were separated from the cob. Both the kernel and the cob were separately extracted by the method of Example 7. Briefly, extraction was performed in 100% methanol for 2 hours at 70° C. The extract was dried under vacuum and redissolved in DMSO and aliquots of about 2 μl, 5 ul and 10 μl were added to cultured MCF-7 cells. After 2 days, the cells were counted.

Figure 17:
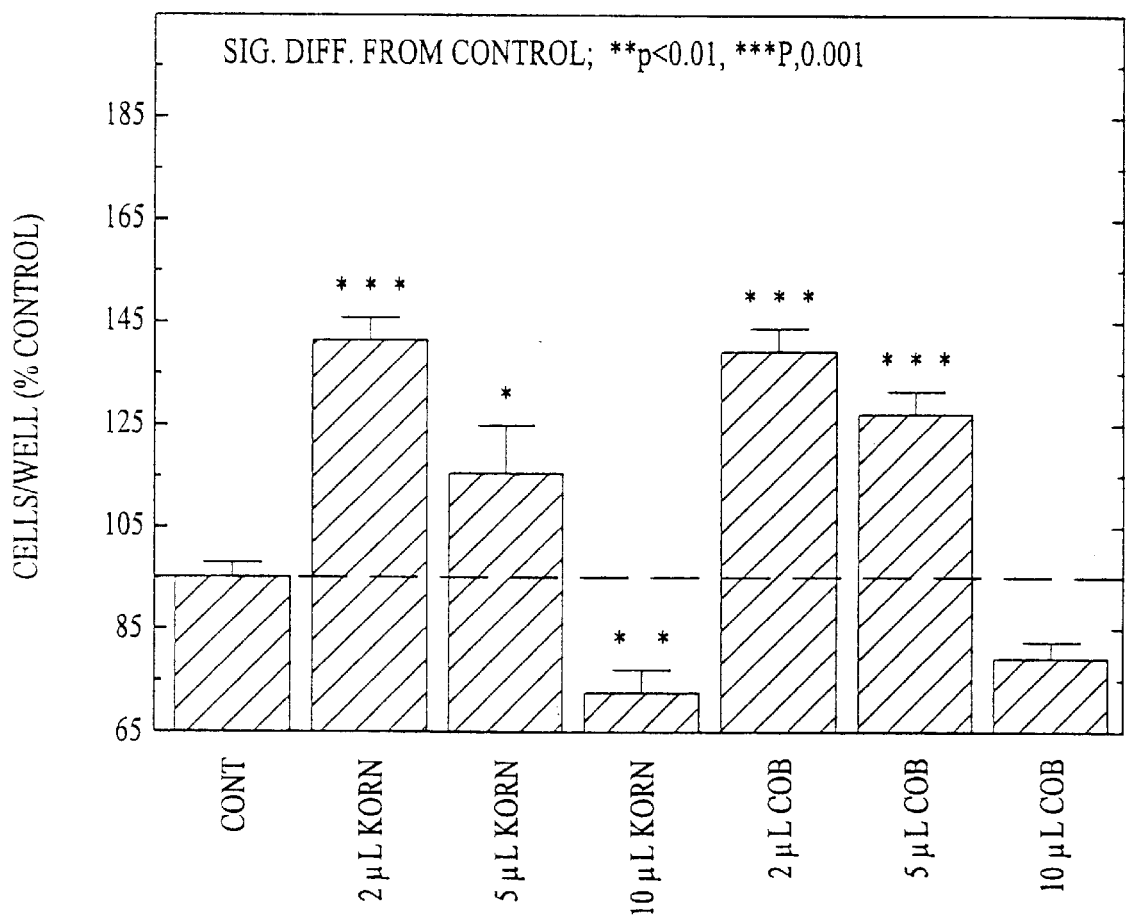
FIG. 17 Effect of extract from fresh corn on cell proliferation.

The data is plotted in FIG. 17. Low doses of either the fresh kernel (Kern) or fresh cob (Cob) extract stimulated MCF-7 human breast cancer cell proliferation relative to controls whereas higher doses of these preparations inhibited cell proliferation. A classical bell-shaped dose response curve was obtained for both the corn cob and corn kernel preparations. This demonstrates that extract from fresh corn on the cob contains a mitogenic activity similar to that described for extract from ground corn cob bedding.

Example 17
Further Purification of GCCB Extract by High Performance Liquid Chromatography.

Figure 18A:
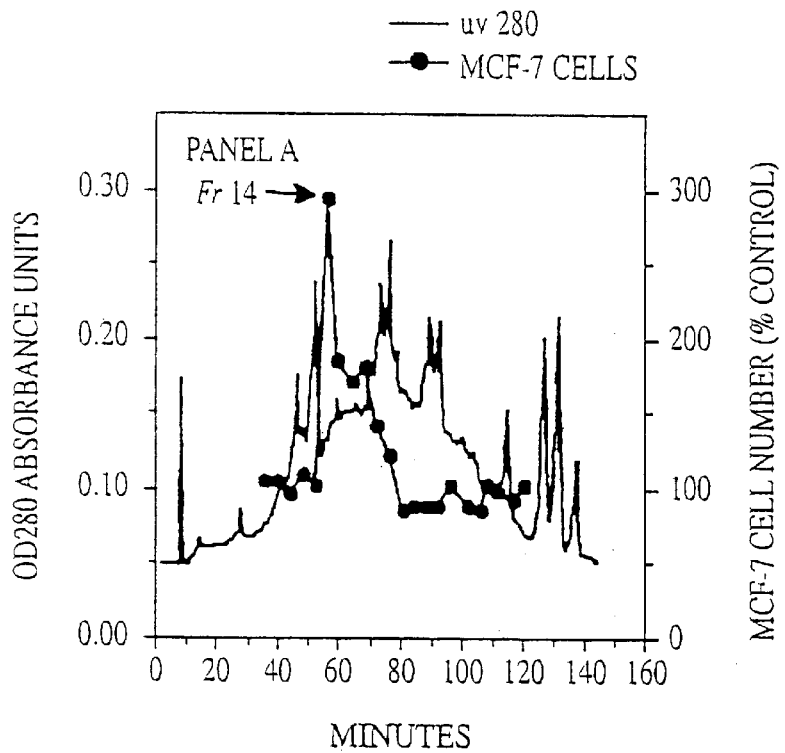
FIG. 18A Purification of mitogenic agent(s) from GCCB extract.
Figure 18B:
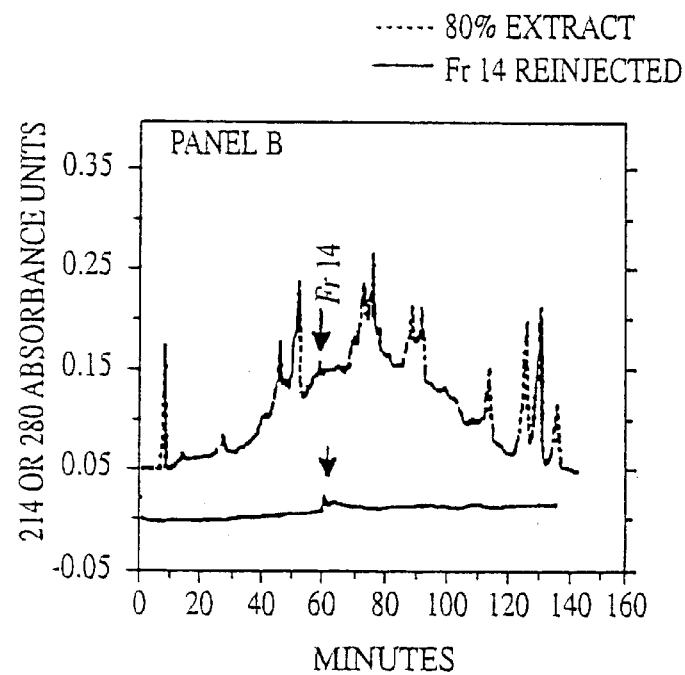
FIG. 18B Re-chromatography of mitogenic agent(s) from GCCB extract.
Figure 19:
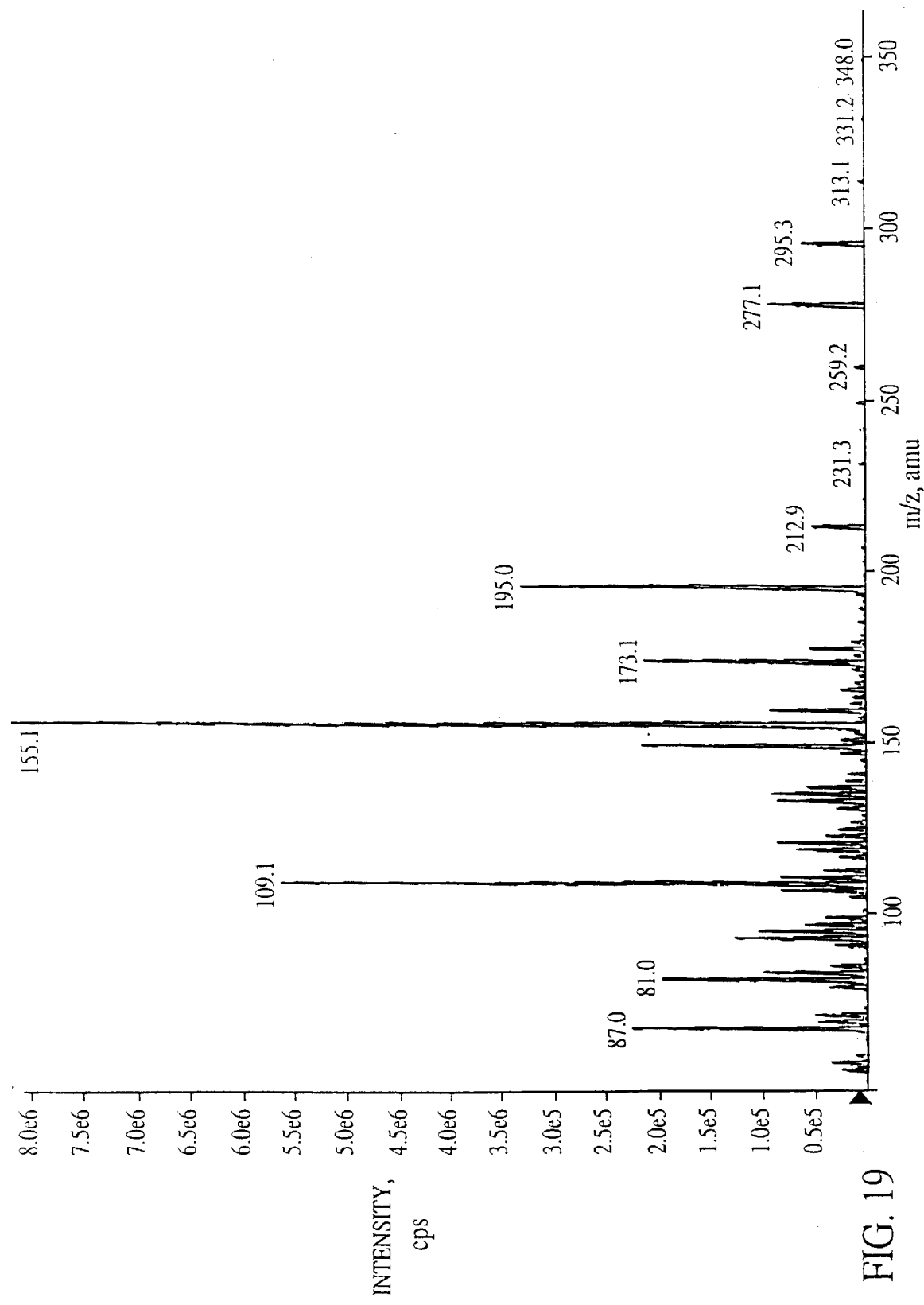
FIG. 19 Molecular weight determination of a putative mitogenic agent(s) in corn cob bedding extract.

An aliquot of the 80% methanol fraction of GCCB extract was injected onto a semi-preparative Altex Ultrasphere-ODS reversed phase column HPLC column (10 mm ID×25 cm length) equilibrated in 70% Solvent A (HPLC grade water containing 0.05% acetic acid) and 30% Solvent B (HPLC grade acetonitrile containing 0.05% acetic acid). The solvent flow rate through the column was 2 ml per minute. Ten minutes following injection of the GCCB preparation, a linear gradient increasing to 65% Solvent B over a 120 minute interval was initiated and the run was continued for 140 minutes. Four minute fractions of the column eluate were collected from injection (time 0) through 140 minutes. Aliquots of the fractions were dried, redissolved in ethanol and added to exponentially growing MCF-7 human breast cancer cells (large filled circles) and cell number was determined 6 days following treatment. The data shown in FIGS. 18A and 19B suggested that the MCF-7 stimulating activity eluted from the column coincident with two very small peaks of UV-absorbing material. In FIG. 11A, the mitogenic activity of Fraction 14 (arrow labeled Fr 14) was not resolved into two components because of the large (four minute interval) fraction size. To confirm multiple components, an aliquot of Fraction 14 was re-injected onto a $C_{18}$ Ultrasphere-ODS column and eluted as described above to check purity. Re-chromatography of Fraction 14, indicated by the solid line in FIG. 18B, revealed that Fraction 14 consisted of two very small UV-absorbing peaks (arrow labeled Fr 14 in FIG. 18B), which co-eluted with the mitogenic activity.

Example 18

Molecular Weight Determination of the Putative Mitogenic Agents in Corn Cob Bedding Extracts by Mass Spectrometry.

Figure 20:
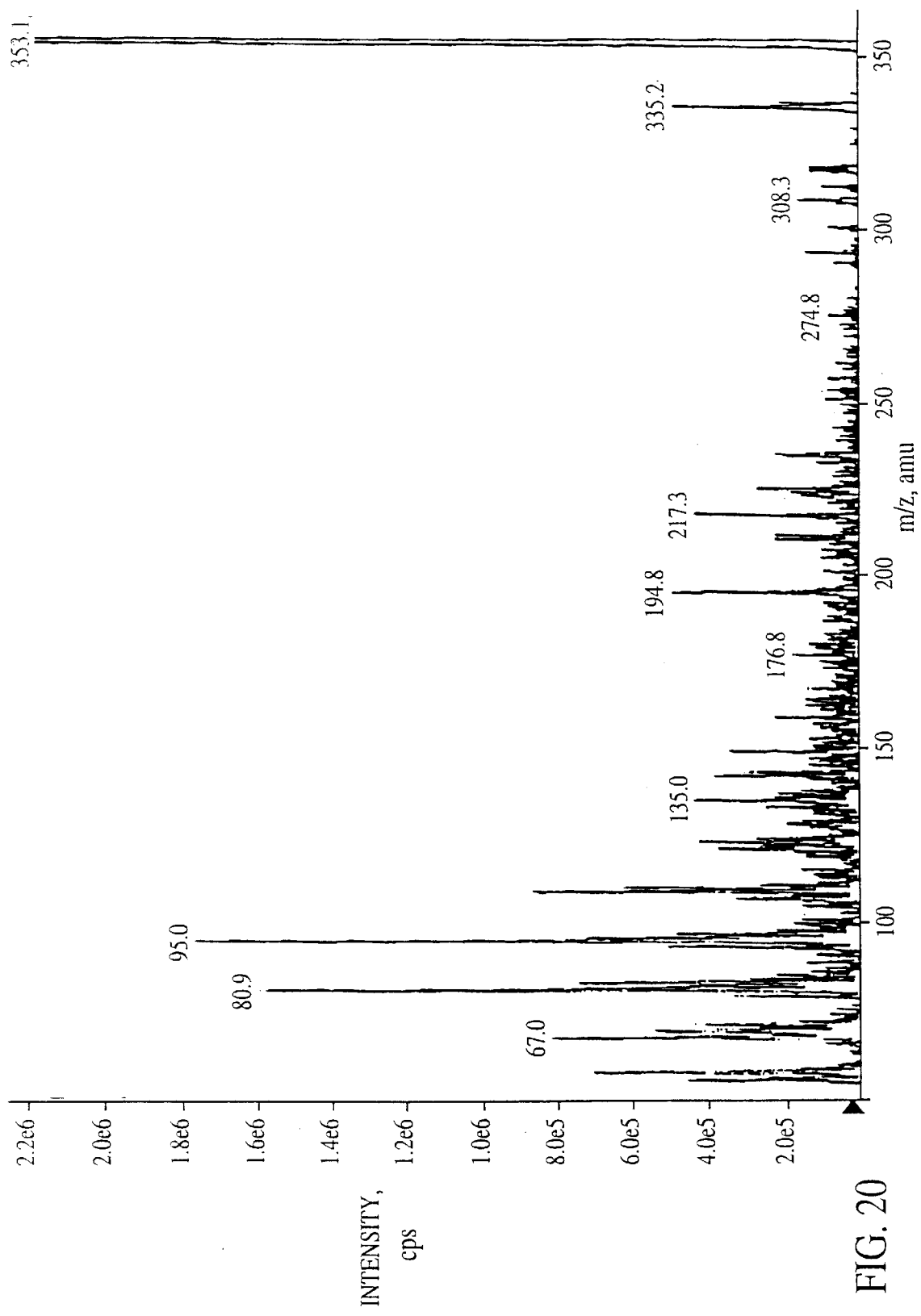
FIG. 20 Molecular weight determination of a putative mitogenic agent(s) in corn cob bedding extract.

An aliquot of the HPLC purified Fraction 14 was diluted in an aqueous mobile phase consisting of 50% acetonitrile containing 4 mM ammonium acetate. This was loop injected at 5 µL per minute onto an API 3000 triple quadrupole mass spectrometer (PE Siex Concord, Ontario, Canada) for mass spectrometric (MS) and tandem mass spectrometric (MS/MS) analysis. Samples were ionized under atmospheric pressure ionization conditions with a skimmer voltage of 70V and the instrument was tuned to detect positive ions. The first quadrupole was scanned to detect ions for MS analysis or held static to transmit selected ions for MS/MS analyses. Collisionally activated decomposition of selected ions was achieved in the rf-only quadrupole collision cell with nitrogen as the collision gas and collision energies between 30 and 60 eV. The third quadrapole was scanned to detect positive ions. The results of this analysis confirmed HPLC studies demonstrating that Fraction 14 contained two substances. The molecular weights of these substances were determined to be 348 amu (FIG. 19) and 353 amu (FIG. 20), respectively. Since these were the only components detected in the preparations, both substances have a high probability of representing the active agents in the GCCB preparations. More sophisticated analysis by gas chromatography-mass spectrometry (GC-MS), infrared spectrometry (IRS) and nuclear resonance spectrometry (NMRS) may be used to determine the chemical structure(s) of the 348 and 353 amu components in the GCCB samples and establish these compounds as the mitogenic agents in cultured breast cancer cells and as the biological activity in behavioral studies with male and female animals studies described above.

Example 19

Confirmation of Two Mitogenic Agents in GCCB Extracts by HPLC.

A sample of GCCB was prepared and chromatographed on HPLC under conditions identical to those described in Example 17 with the exception that fractions were collected at one minute intervals instead of four minute intervals. The smaller fraction size increased the resolution of the components four fold as opposed to pooling fractionated material over four minute intervals as was done in Example 17. Aliquots of each of the fractions were assayed for mitogenic activity in MCF-7 human breast cancer cells as was described for Examples 7, 8 and 10. The data, shown in FIG. 21, clearly demonstrate that two peaks of mitogenic activity eluted from the column coincident with corresponding peaks of UV-absorbing material. These two agents likely represent the 348 and 353 molecular weight components observed by HPLC-MS analysis, shown in FIGS. 19 and 20, respectively, and are strong candidates for the active components in the GCCB extract preparations.

Other embodiments and uses of the invention will be apparent to those skilled in the art from consideration of the specification and practice of the invention disclosed herein. All U.S. and foreign patents and patent applications, including the provisional patent application, Ser. No. 60/087,680, filed Jun. 2, 1998, and all other documents referenced herein, for whatever reason, are specifically incorporated by reference. The specification and examples should be considered exemplary only with the true scope and spirit of the invention indicated by the following claims.

We claim:

1. A process for producing an antineoplastic substance comprising:

extracting a *Zea mays* plant product in a first solvent to produce a solvent extract, wherein said *Zea mays* plant product is selected from the group consisting of corn kernel, corn cob, animal bedding material made from corn cob, and mixtures thereof and wherein said first solvent comprises a solar solvent;

drying said solvent extract to produce an extracted solid;

solubilizing said extracted solid in a second solvent;

purifying said solubilized extract in a chromatographic process;

collecting an active fraction from said chromatographic process said active fraction being the antineoplastic substance and having antineoplastic activity.

2. The process of claim 1 wherein said animal bedding material is ground corn cob bedding.

3. The process of claim 1 wherein said first solvent is selected from the group consisting of alcohols, ethers, ketones, water and mixtures thereof.

4. The process of claim 3 wherein said alcohol is methanol.

5. The process of claim 1 wherein said first solvent and said second solvent are the same.

6. The process of claim 1 wherein said extracting step is from 1 hour to 1 month.

7. The process of claim 1 wherein said extraction step is carried out at a temperature between 0° C. and 100° C.

8. The process of claim 1 wherein said chromatographic process is a procedure selected from the group consisting of column chromatography, batch chromatography, precipitation, specific adsorbent chromatography, gel filtration, and combinations thereof.

9. The process of claim 8 wherein said column chromatography is a reverse phase chromatography column comprising a $C_{18}$ solid phase and a methanol/water liquid phase.

10. The process of claim 1 wherein said active fraction is a fraction of about 80% methanol.

11. The antineoplastic substance produced by the process of claim 1.

12. A pharmaceutical preparation comprising the antineoplastic substance produced by the process according to claim 1 and a pharmaceutically acceptable carrier.

13. The pharmaceutical preparation of claim 12 prepared in the form of an aqueous solution.

14. The pharmaceutical preparation of claim 13 wherein said aqueous solution is for oral use or parenteral use.

15. The pharmaceutical preparation of claim 12 prepared in the form of capsules for oral use.

16. The pharmaceutical preparation of claim 12 prepared in the form selected from the group consisting of unguents, ointments, creams, suppositories and ovules.

17. A method for treating a patient with a neoplastic disorder comprising administering to the patient an antineoplastic composition comprising an effective quantity of the antineoplastic substance of claim 1.

18. The method of claim 17 wherein said antineoplastic composition further comprises an antineoplastic compound.

19. The method of claim 18 wherein said antineoplastic compound is methotrexate.

20. The method of claim 18 wherein said antineoplastic compound is selected from the group consisting of 5-fluorouracil, 6-mercaptopurine, 6-thioguanine, alkylating agents, androgens, antiadrenals, antiandrogens, antiestrogens, antimetabolites, asparaginase, bleomycin, busulfan, carboplatin, carmustine, chlorambucil, cisplatin, corticosteroids, cyclophosphamide, cytarabine, dacarbazine, dactinomycin, daunorubicin, doxorubicin, estrogens, etoposide, fludarabine, fluorouracil, flutamide, hexamethylmelamine, hormones, hydroxyurea, hypothalamic agents, idarubicin, ifosfamide, intrapleural, lomustine, mechlorethamine, melphalan, methotrexate, mithramycin, mitomycin, mitotic inhibitors, mitoxantrone, pacelitaxel, procarbazine, progestins, streptozocin, taxol, thiotepa, vinblastine, vincristine, vinorelbine and combinations and analogs thereof.

21. The method of claim 17 wherein said neoplastic disorder is selected from the group consisting of prostate cancer, breast cancer, lymphoma, leukemia, testicular cancer, gastrointestinal tract cancer, lung cancer, skin cancer, head tumors, neck tumors, bone cancer, liver cancer, and pancreatic cancer.

22. The method of claim 17 further comprising the step of administering an antineoplastic compound.

23. The method of claim 22 wherein the antineoplastic compound is methotrexate and the neoplastic activity is breast cancer cell proliferation.

24. The method of claim 17 wherein the extract is administered orally, topically, intramuscularly, intravenously, subcutaneously, vaginally, rectally, or by pulmonary absorption.

25. An antineoplastic substance produced by a process comprising the steps of extracting a *Zea mays* plant product in a first solvent to produce a solvent extract, wherein said *Zea mays* plant product is selected from the group consisting of corn kernel, corn cobs animal bedding material made from corn cob, and mixtures thereof, and wherein said first solvent comprises a solvent selected from the group consisting of alcohols, ethers, ketones, water and mixtures thereof;

drying said solvent extract to produce an extracted solid;

solubilizing said extracted solid in a second solvent;

purifying said solubilized extract in a chromatographic process;

collecting an active fraction from said chromatographic process, said active fraction being the antineoplastic substance and having antineoplastic activity.

26. A method of inhibiting neoplastic activity comprising administering an effective amount of the antineoplastic substance of claim 25 to tissues or cells.

27. A method of treating an individual with a neoplastic disorder comprising administering to the individual an effective amount of the antineoplastic substance of claim 25.

\* \* \* \* \*